(12) United States Patent
John

(10) Patent No.: US 12,179,033 B1
(45) Date of Patent: *Dec. 31, 2024

(54) NEUROSTIMULATION TREATMENT FOR ABNORMAL CONNECTIVITY WITH A CINGULATE REGION

(71) Applicant: Michael Sasha John, Larchmont, NJ (US)

(72) Inventor: Michael Sasha John, Larchmont, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/465,435

(22) Filed: Sep. 12, 2023

Related U.S. Application Data

(63) Continuation of application No. 17/812,336, filed on Jul. 13, 2022, now Pat. No. 11,779,775, which is a continuation of application No. 15/286,372, filed on Oct. 5, 2016, now Pat. No. 11,389,661, which is a continuation of application No. 13/213,076, filed on Aug. 18, 2011, now abandoned, which is a continuation-in-part of application No. 11/309,835, (Continued)

(51) Int. Cl.
| | |
|---|---|
| *A61N 2/00* | (2006.01) |
| *A61B 5/026* | (2006.01) |
| *A61B 5/055* | (2006.01) |
| *A61N 5/00* | (2006.01) |
| *A61N 5/04* | (2006.01) |
| *A61N 1/05* | (2006.01) |
| *A61N 1/36* | (2006.01) |
| *A61N 1/372* | (2006.01) |

(52) U.S. Cl.
CPC .......... *A61N 2/006* (2013.01); *A61B 5/0263* (2013.01); *A61B 5/055* (2013.01); *A61N 2/00* (2013.01); *A61N 2/002* (2013.01); *A61N 2/004* (2013.01); *A61M 2230/10* (2013.01); *A61N 1/0529* (2013.01); *A61N 1/0534* (2013.01); *A61N 1/36025* (2013.01); *A61N 1/36082* (2013.01); *A61N 1/36103* (2013.01); *A61N 1/37247* (2013.01)

(58) Field of Classification Search
CPC .......... A61N 2/00; A61N 2/002; A61N 2/004; A61N 2/006; A61N 1/36025; A61N 1/36082; A61B 5/0263; A61B 5/055
See application file for complete search history.

(56) References Cited

U.S. PATENT DOCUMENTS

| | | | |
|---|---|---|---|
| 2003/0006770 A1* | 1/2003 | Smith | G01R 33/56 324/309 |
| 2004/0092809 A1* | 5/2004 | DeCharms | A61B 5/0048 600/410 |

(Continued)

*Primary Examiner* — Pamela M. Bays
(74) *Attorney, Agent, or Firm* — Rosenberg, Klein & Lee

(57) ABSTRACT

A method to guide a targeted neurostimulation to the brain of a patient. Neuroimaging data is sensed from the brain of the patient. A processor is used to evaluate the neuroimaging data in order to calculate result data for a modeled functional measure of a particular brain network which defines a first brain region and a second brain region. A target location is determined in the first brain region based upon the result data and a functional connection measure between first and second brain region. A transcranial magnetic stimulator is adjusted to provide a magnetic stimulation signal for stimulation of the target location.

28 Claims, 10 Drawing Sheets

Related U.S. Application Data filed on Oct. 9, 2006, now Pat. No. 8,027,730, which is a continuation of application No. 11/308,440, filed on Mar. 24, 2006, now Pat. No. 7,894,903.

(60) Provisional application No. 60/594,270, filed on Mar. 24, 2005.

(56) References Cited

U.S. PATENT DOCUMENTS

| | | | |
|---|---|---|---|
| 2005/0049651 A1* | 3/2005 | Whitehurst | A61N 1/36096 607/45 |
| 2006/0212091 A1* | 9/2006 | Lozano | A61P 43/00 607/45 |

* cited by examiner

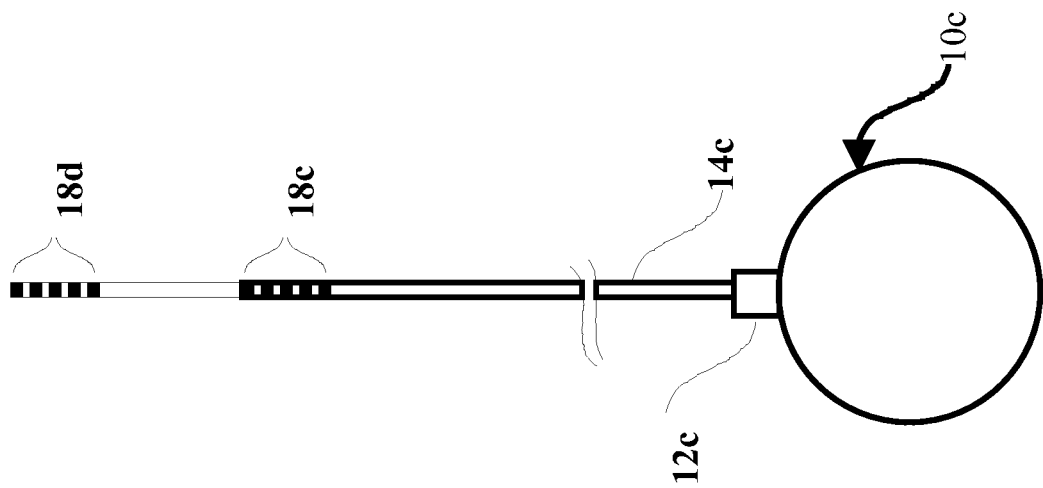
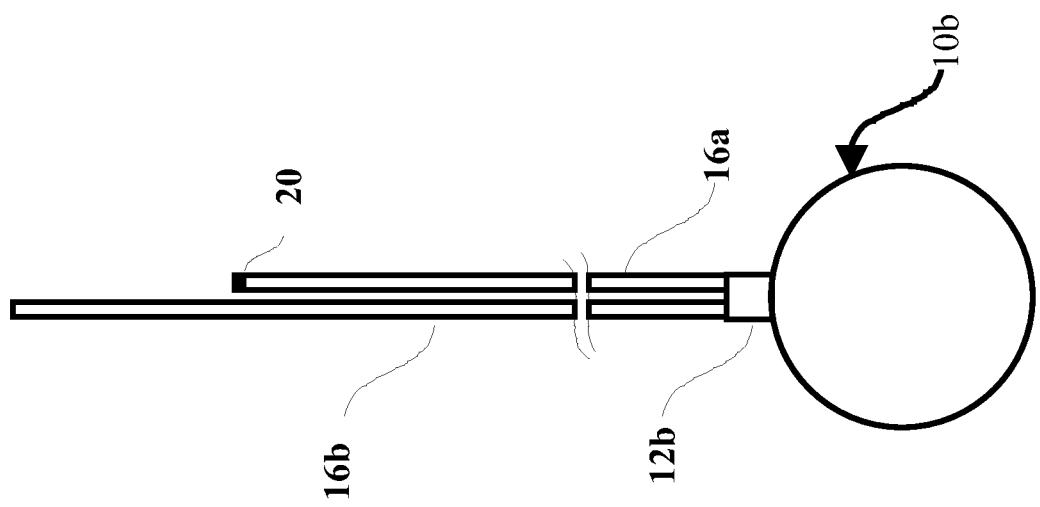
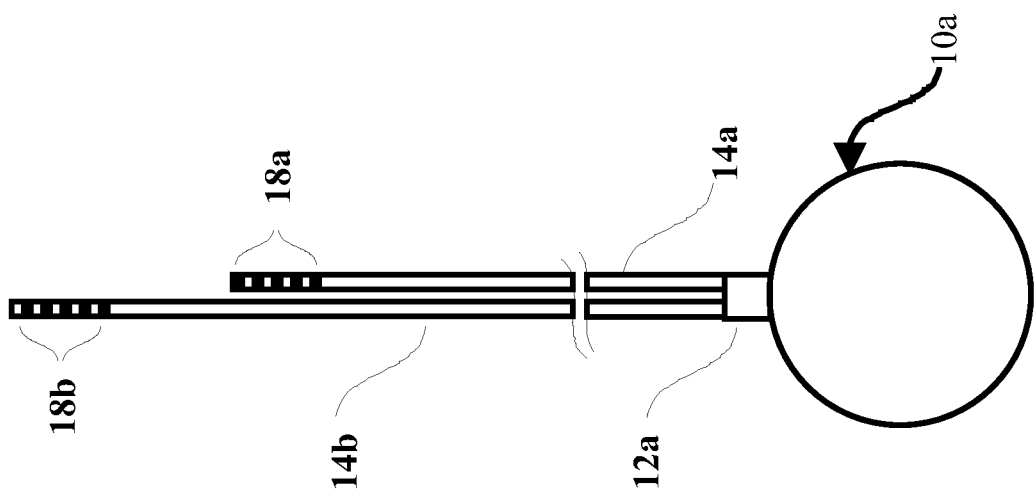

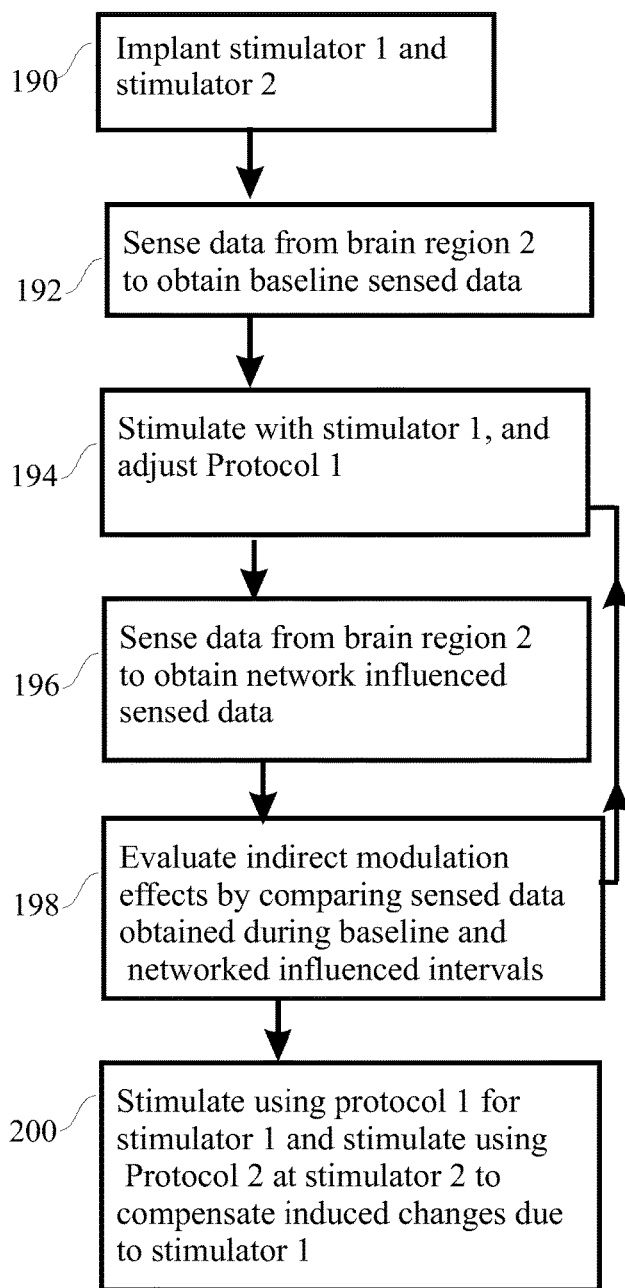
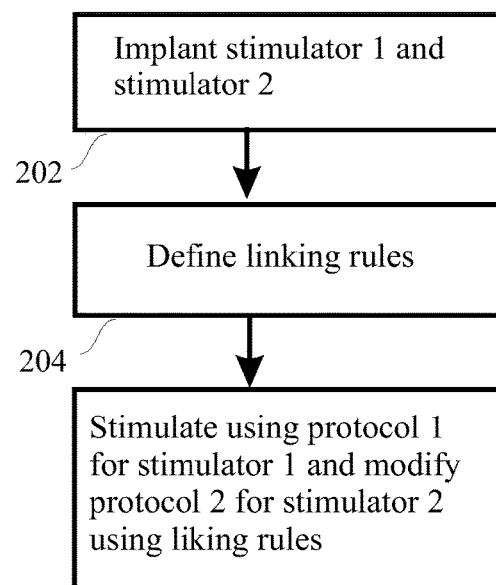
FIG 2I
FIG 2J

     
   
FIG 3A    FIG 3B    FIG 3C    FIG 3D
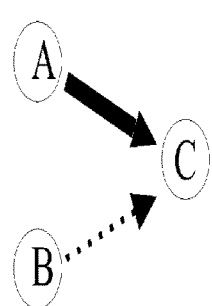 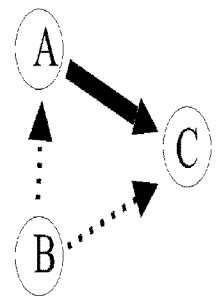 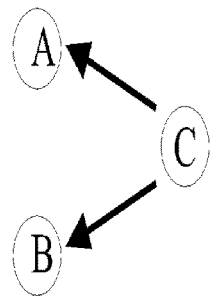
FIG 3E    FIG 3F    FIG 3G

NEUROSTIMULATION TREATMENT FOR ABNORMAL CONNECTIVITY WITH A CINGULATE REGION

CROSS REFERENCE TO RELATED APPLICATIONS

This application is a continuation of Ser. No. 17/812,336 filed on Jul. 13, 2022, now U.S. Pat. No. 11,779,775 B1 which is a continuation of Ser. No. 15/286,372, filed on Oct. 5, 2016, now U.S. Pat. No. 11,389,661 B2 which is a continuation of U.S. application Ser. No. 13/213,076, filed on Aug. 18, 2011 entitled "Systems and Methods for Treating Disorders of the Central Nervous System by Modulation of Brain networks" which is a continuation-in part of U.S. application Ser. No. 11/309,835 filed on Oct. 9, 2006, now U.S. Pat. No. 8,027,730 entitled "Systems and Methods for Treating Disorders of the Central Nervous System by Modulation of Brain networks" which is a continuation of U.S. application Ser. No. 11/308,440 filed on Mar. 24, 2006, entitled "Systems and Methods for Treating Disorders of the Central Nervous System by Modulation of Brain networks" now U.S. Pat. No. 7,894,903, which was based upon provisional application Ser. No. 60/594,270 filed on 24 Mar. 2005, the complete disclosures of which are hereby incorporated by reference in the entirety.

FIELD OF THE INVENTION

The invention relates to modulation of the central nervous system for treating brain disorders and more particularly to modulation of brain networks associated with undesirable aspects or symptoms of a patient's brain disorder.

BACKGROUND OF THE INVENTION

Various disorders of the central nervous system affect millions of people annually. While a large proportion may be aided by pharmaceutical interventions, many are not helped by medication, or are not helped sufficiently to provide desired levels of relief. In depression, for example, up to ⅓ of patients may be either partially or completely resistant to treatment. Further, choosing and adjusting the medications used for treatment of brain disorders, such as attention deficits with or without hyperactivity, developmental, psychiatric, mood, and neurological disorders is a complicated process with unwanted side-effects often occurring simultaneously with treatment benefits.

A number of novel technologies for assisting treatment resistant patients have recently become commercially available. Implantable neurostimulators, providing electrical or pharmaceutical therapy are available from companies such as Medtronic, Advanced Neuromodulation Systems, Cyberonics, and NeuroPace. These neurostimulators are used to treat a wide variety of medical conditions including movement disorders, epilepsy, pain, depression, and other disorders of the central nervous system. In addition to direct electrical/pharmaceutical stimulation of brain tissue, transcranial magnetic stimulation and vagus nerve stimulation have also shown moderate efficacy with respect to treatment of brain disorders such as depression, migraine, and epilepsy.

Neuromodulation for treatment of brain disorders, such as movement disorders, is quite promising and over the last 2 decades has been carried out with increasing rates of success (Cooper et al, 1982). For example, recently, Yianni et al (2005) reported successful treatment of 5 subjects suffering from dystonia by means of deep brain stimulation (DBS) of the globus pallidus. Psychiatric disorders are likely more complex than this type of pain disorder and will require more complicated neuromodulation regimens in order to successfully treat at least a portion of patients. For example, Abelson et al (2005) explored using bilateral DBS of the anterior limbs of the internal capsule, rather than ablative surgery, for treatment of refractory obsessive-compulsive disorder (OCD), and found that only two of the four patients were aided, while only one of these showed a significant improvement. In another study, Mayberg et al (2005), investigated DBS for treatment-resistant depression, and found striking and sustained improvement in mood in 4 of the 6 patients, while 2 patients did not obtain benefit of the intervention. These investigators chose their neuromodulation target based upon positron emission tomography (PET) data which suggested that, in addition to other abnormalities, the subgenual cingulate region (Brodmann area 25) was metabolically overactive in treatment-resistant depression. Accordingly, treatment consisted of modulating this area with DBS to provide inhibitory electrical stimulation and decrease this excessive neural activity. While treatment successfully decreased activity in the target area in all patients, this did not lead to improvement of unwanted behavioral symptoms in 2 of the 6 patients. This suggests treatment will entail a more complicated mechanism than a simple on-off switch specific to a particular isolated neural target. Further evidence that complex disorders will not always benefit from simple DBS treatment paradigms comes from Schoenen et al (2005), who attempted treatment of 6 patients with chronic cluster headaches using DBS of the ipsilateral ventroposterior hypothalamus. Two patients showed considerable improvement, while 3 patients did not show improvements and 1 died due to complications during surgery: DBS is not a minor treatment option. Neuromodulation systems and methods can certainly still benefit from considerable improvement when used for the treatment of many disorders of the central nervous system.

While these studies each targeted a specific brain region for neuromodulation treatment (although sometimes bilaterally), the imaging data revealed that stimulation caused modulation of activity in several areas distal from the site of stimulation: neuromodulation of target sites affected other areas of brain networks within which the target site existed. In the Yianni (2005) study, for example, DBS, (or absence of DBS) of the globus pallidus showed consistent activation (or hypo-activation) in several brain areas that were distinct from the site of stimulation. This provides evidence that treatment of a target region that is related to a motor disorder may modulate at least 2 or 3 regions of a brain network, each of which may, or may not, be related to the disorder. Similarly, Mayberg and colleagues (2005) found changes in downstream limbic and cortical sites (e.g., areas BA10, BA9/46, BA24, BA6, BA40), when stimulation of the target site led to successful treatment response. Interestingly, both post-treatment responders and non-responders showed decreased cerebral blood flow in the target neural region (Mayberg 2005). Accordingly, differential treatment effects might be due to other areas of a brain network being affected by or adapting to changes in the target brain region.

Support for such network effects has come from neuroimaging data which has shown that several brain areas seem to be part of brain networks underlying different characteristics of major depressive disorder (Bench, 1993; Baker, 1997; Mayberg et al, 2004). Producing a desired change in the target area may lead to changes in other areas, at least under some conditions, and these other changes can be responsible for side effects, treatment, or treatment resistance. However, these studies and other prior art do not describe or anticipate methods of improving treatment by stimulating multiple areas of the network to compensate for interactions that may occur between different regions of the network. The prior art has described either stimulating a target location, or stimulating several target locations independently, but does not consider the role of these targets within a brain network that contributes to at least one characteristic of a disorder. There is no consideration of the influence of the stimulation on other locations of the network.

SUMMARY OF THE INVENTION

The current invention recognizes, addresses, and utilizes the interactions and connectivity that exists between different brain regions of a brain network to provide improved treatment. Information about interactions between brain structures is used to guide the adjustment of neurostimulation parameters of the treatment protocol. For example, linking rules can be used to increase inhibitory stimulation at a first area when stimulation is provided at a second area, wherein the stimulation at second area has shown to produce unwanted increase in the activity of the first area. Further, network considerations can also be used to guide the evaluation of sensed data. In relation to sensing, the data sensed from a first brain area can be evaluated differently when stimulation is occurring in a second brain area, then when it is not. The use of linking rules to guide methods of stimulation and evaluation of sensed data is a novel advantage of the invention. The present invention thus provides DBS treatment that adjusts for the activation of multiple regions of a network which may or may not be stimulated directly. Further, it uses neuromodulation methods that control (e.g., rebalance) the relative activation levels of different areas of the network. Successful treatment should rely upon neuromodulation protocols that take into account (e.g., compensate for) the cascade of effects which stimulation of a particular target area may have within the larger context of the brain networks in which it is a part.

It is an object of the invention to provide neurostimulation of brain networks (NBN) by utilizing a stimulation protocol that uses linking rules to adjust the stimulation provided at one target region according to the neurostimulation provided at a different target region, where both regions are part of a brain network.

It is another object of the invention to provide a method of treatment wherein target brain regions are selected and treated based upon characteristics of brain networks in which they participate.

It is another object of the invention to provide methods and systems for neuromodulation, control, and responsive neuromodulation which provide for observing, evaluating and utilizing information about the relative activity of two or more areas of a brain network to provide treatment.

It is another object of the methods and systems of the invention to provide NBN to one or more areas based upon the functional or anatomical connectivity of two or more areas of a brain network.

It is another object of the invention to independently treat different symptoms of the disorder by directed neuromodulation of a brain network.

It is another object of the invention to provide a method of neuromodulation of several brain areas using a neuromodulation protocol which incorporates the fact that these modulate each other, for example, by compensating for connections between brain structures.

It is another object of the invention to provide a method of neuromodulation of multiple areas of a brain network so that the relative activations, drug levels, or other characteristics are controlled in a desired manner.

It is another object of the invention to provide a method of neuromodulation of multiple areas of a brain network by modulating two or more brain target regions included in a brain network underlying the disorder, wherein stimulation in one brain target is modified, at least in part, based upon stimulation in another of the targets.

It is another object of the invention to provide a method of neuromodulation of two or more areas of a brain network underlying the disorder, wherein the activity of at least one brain region is modulated in relation to the activity sensed for at least a second brain region.

It is another object of the invention to provide a method of neuromodulation which includes implanting stimulation leads in at least two anatomically distinct brain regions, both of which are involved in a network implicated in a disorder, and stimulating these leads to modulate the network in a desired manner, or to normalize the activity of the network.

It is another object of the invention to provide a method of neuromodulation which includes treating different characteristics of a disorder by adjusting stimulation in different regions of a network.

It is another object of the invention to provide a method of neuromodulation which uses linking rules to link the neuromodulation protocol of one stimulated area to those used at a different modulated area.

It is another object of the invention to provide a method of neuromodulation which comprises alternating between two or more target brain regions of a network to deter the emergence of adaptation and neural compensation as may occur, for example, via endogenous homeostatic mechanisms (e.g., pruning, receptor up-/down-regulation).

It is another object of the invention to provide a method of neuromodulation of multiple areas of a brain network which includes quantifying the interaction between two elements in a network and compensating for this during treatment.

It is another object to decrease the risk of unwanted adaptation to neuromodulation treatment by stimulating two or more neural targets of a brain network.

These and other objects will be described in this specification, drawings, and claims, and will provide systems and methods of neuromodulation which will greatly improve treatment of various brain disorders.

BRIEF DESCRIPTION OF THE DRAWINGS

The features and advantages provided by the invention will become further apparent from the detailed description below and the accompanying drawings, in which:

FIG. 1A shows a preferred embodiment of an implanted brain modulation system for providing electrical neuromodulation to two distinct brain regions.

FIG. 1B shows an alternative example of an implanted brain modulation system for providing either electrical or drug neuromodulation, or both to two distinct brain regions.

FIG. 1C shows another alternative embodiment of an implanted neuromodulation system, for providing electrical neuromodulation

FIGS. 2B to 2J show examples of flowcharts for alternative methods of treatment of brain disorders.

FIG. 3A illustrates a network model which does not incorporate information about interactions or connections which putatively exist between two brain structures, or where these in fact do not exist.

FIGS. 3B to 3G show alternative examples of brain network models comprised of two or more brain structures, which show the influence that each structure has on the other as well as the direction, type, and strength of the influence.

DETAILED DESCRIPTION

Figure 2A:
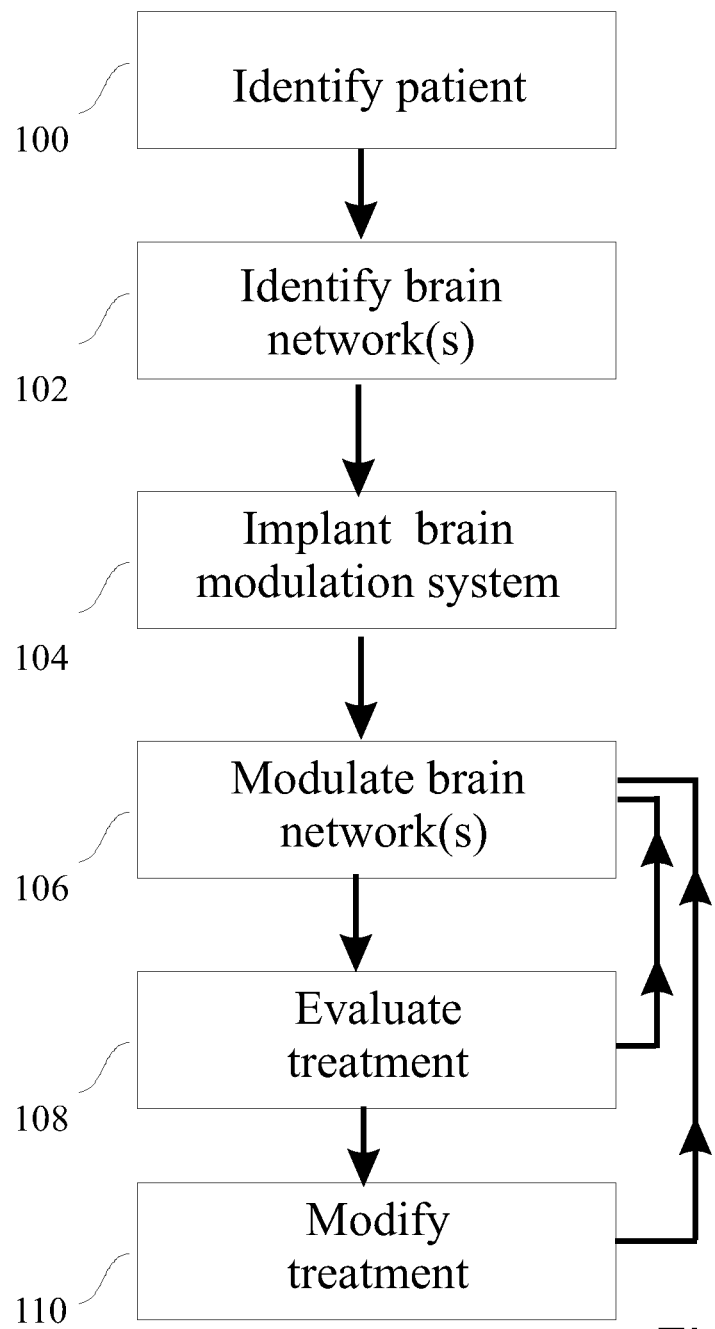
FIG. 2A shows a general example flowchart of a preferred method of treatment of brain disorders.

The systems and methods will now be described in greater detail, with reference to detailed illustrative embodiments. It will be apparent that systems and methods of the invention may be embodied and modified in a variety of manners without departing from the scope and spirit of the description. The following material provides definitions for terms used in this application. However, these terms may be expanded upon and/or modified according to the various specific alternative embodiments which will be described As used herein, "brain modulation system (BMS)" refers to a system which provides neuromodulation of brain networks. The BMS may be realized using a "brain neuromodulation device" (BND), for example, an apparatus such as an implantable neurostimulator, drug pump, or an instrument which provides for both electrical and drug delivery. The BND may be a commercially available generic device which can be adapted to approximately achieve the intended neuromodulation of a brain network as described herein. A BMS can also utilize a BND which is a transcranial magnetic stimulator to provide magnetic stimulation. A BMS can be realized completely within a BND, but may also exist in a distributed fashion. For example, the BND may communicate with an external patient programmer which can be used to program the BND, and which comprises a part of the BMS. The BMS, and its methods, can include the utilization of sensed data which is sensed by external instrumentation such as an MRI (magnetic resonance imaging) scanner. BNDs can be implantable devices, can be partially or completely external, and can be devices which are affixed within the skull.

As used herein, the terms brain-"network", "pathway", or "circuit", refer to two or more brain regions for which at least first brain area has been shown to modulate at least a second brain area. A brain network which that is identified for treatment would normally contain at least one brain area that has been associated with a symptom for which therapy is sought. A symptom can be, for example, an undesirable behavioral, emotional, cognitive, brain or sensory process or state. A brain network can also be comprised of several divisions (i.e., nuclei, or a specialized group of cells), within a particular brain structure, such as the thalamus, since divisions within a structure can modulate activity in other divisions of that structure, either directly, or via a multi-synaptic pathway. A network can be considered pathological when it is associated with a brain disorder. The pathology can be reflected, for instance, by sensed data which is evaluated relative to a threshold, or in relation to normal, expected, or desired activity, as may be defined by treatment criteria.

As used herein, "brain disorder" refers to at least one characteristic or symptom of a psychiatric, mood, neurological, movement, epilepsy, behavioral, addiction, attention, consciousness (e.g., coma), psychological, or other central nervous system disorder. The brain disorder can also be a thought processes disorder, memory disorder, "mental disorder", age-related disorder, cognitive or other disorder of neural origin. Brain disorders can also include pain disorders, migraine, headache, stroke, and other types of traumatic brain injury. The psychiatric disorders can include, for example, forms of psychosis, anxiety disorders, schizophrenia, and obsessive-compulsive disorder. Rather than being defined by a particular behavior or DSM criteria, a brain disorder may be defined as an abnormality as may be evidenced from analysis of neuroimaging data, such as an abnormal EEG or QEEG profile. This abnormal activity may be associated with structures of a relevant network using source analysis methods.

As used herein, the term "neuroimaging" can refer to either functional or structure neuroimaging. The term "sensing" includes performing sensing using neuroimaging.

As used herein, the term "functional neuroimaging", refers to any method which provides information about an amount, or changes in amount, of brain a characteristic including blood flow, neurotransmitter level, metabolism, electrophysiological activity, and includes information obtained from either acutely/chronically implanted sensors or external sources. Functional neuroimaging includes implanted electrodes or other sensors which provide estimates of neurophysiology/neurochemistry/metabolism or other measure correlated with the function of brain regions. Further, functional neuroimaging can include techniques such as electroencephalography (EEG) obtained from either scalp or implanted electrodes, magnetoencephalography (MEG), evoked-potential (EP), functional magnetic resonance imaging (fMRI), and other magnetic resonance imaging techniques such as magnetic resonance spectroscopy (MRS). Functional neuroimaging includes analysis of neuroimaging data according to conventional techniques known to those skilled in the art. Further, neuroimaging (and collection of self-norms) can occur before, during, and/or after surgery, and can occur when a patient is resting, engaged in a cognitive, emotional and/or other task, and can occur while patients are exposed to medication and/or while drug free. Neuroimaging may occur using one or more tasks to assess different symptoms related to the disorder, for example, one task can pertain to measurement of sadness or anxiety, while another can assess hopelessness.

As used herein, the term "structural imaging" refers to any process that provides information about the structure of the brain, including MRI and diffusion tensor imaging (DTI), and CAT-scan, or other methods related to function such as SPECT or MRS.

As used herein "treatment protocol" refers to the protocol used by the treatment program to provide treatment. The treatment protocol has parameters which define the locations for sensing and stimulating operations, and can contain parameter values for the sensing protocol, the stimulation/modulation protocol, and the evaluation protocol. The treatment protocol defines the treatment criteria, the reference values, the linking rules, and any other parameter value which is used to provide specific neuromodulation treatment. A treatment protocol can be designed to cause the treatment program to directly modulate regions of the brain network, or the regions to be modulated can be modulated indirectly by stimulation of neural targets in a different area.

As used herein the terms "sensing protocol/parameters" define how sensing is accomplished and can include placement of sensors, measurement of sensed data including when, if, and what data is sensed, and how the sensed data is processed. The sensing protocol determines the sensing parameters, for example, sensing rate, type, and location. Sensing protocols, including processing of sensed data, can be guided by linked rules. Sensing operations are provided by the sensing subsystem.

As used herein the terms "modulation-protocol/parameters" and "stimulation-protocol/parameters" define how stimulating is accomplished and can include placement of stimulators, stimulation/modulation protocols including when, if, for how long neural regions are stimulated, and which stimulation signals are used to stimulate one or more brain regions. The "parameters" refer to the settings used while achieving the protocol. The stimulation protocol determines the stimulation parameters, for example, stimulation rates, type of one or more drugs to be delivered, dosage, and location. The stimulation protocol can be completely predefined or can also include providing modulation based upon evaluation of sensed data, using data as a control signal. Stimulation operations are provided by the stimulation subsystem.

As used herein the terms "evaluation protocol/parameters" define how sensed data is evaluated. For example, the evaluation protocol defines if the data are compared to reference values such as self-norms, population norms, or selected threshold values. Evaluation of sensed data can be non-statistical, involving simply the utilization of the data to create a stimulation signal using control laws or filters. The evaluation protocol selects treatment criterion according to the treatment protocol, determines how sensed data are compared to reference values using treatment criterion, Evaluation operations are normally provided by the control subsystem. Further, as used herein, the terms "evaluate the sensed data", "evaluate treatment", "data analysis", "analysis protocol", can refer to the methods and protocols used analyze the sensed data. Data analysis can include the step of "processing sensed data" which can refer to signal processing of the sensed data, and processing of the sensed data which converts it into meaningful units. "Using sensed data" can entail simple processing of the data. An, example of using sensed data is feeding it through a circuit to create a stimulation signal, as may occur using control laws. Evaluating the sensed data can comprise several different types of processing including, assessing the sensed data using a criterion which is either met or failed, performing a statistical assessment relative to reference values stored in the database, using measurements of the sensed data in an equation, model, correlation analysis, or algorithm, which provides result data.

As used herein the terms "control protocol/parameters" refers to the subroutine of the treatment protocol that determines what to do if the treatment criterion is met or not met.

As used herein "reference values" refer to values such as self-norms or population norms, values determined by an equation, fixed values, percentage values, or ratio values.

As used herein, the terms "modulate" and "stimulate" (and hence "neuromodulation" and "neurostimulation") refer to causing a change in brain activity, chemistry, or metabolism. The change can refer to an increase, decrease, or even a change in a pattern of neuronal activity. Neurostimulation may be either excitatory or inhibitory stimulation, and may be at least electrical, magnetic, optical or chemical, or a combination of two or more of these. When two or more regions are stimulated, one type of stimulation can be excitatory while the other is inhibitory. When used in context of chemical stimulation, the modulation can include increasing, decreasing, or altering endogenous levels of neurochemical substances or their metabolism, or rates or amounts of their release or reuptake, and can also include dispensing agonists, antagonists, competitive antagonists, precursors and other agents which may modulate the function of endogenous substances and processes.

As used herein, the term "stimulation subsystem" refers to all components that permit the BMS to actively alter ('modulate') neural tissue during neuromodulation treatment, and may include at least one pulse generator, drug delivery apparatus, and any circuits or valves that permit stimulation to occur in a controlled fashion. The stimulation subsystem can utilize, for example, electrical or drug stimulation and can also utilize optical stimulation, which may be transmitted into the brain using fiber-optics. The stimulation subsystem can also rely partially or fully upon external instrumentation such as transcranial magnetic stimulation.

As used herein, the terms "stimulator" refers to any apparatus which permits the transfer of at least electrical, pharmaceutical, optical influences or a combination of these from the BND to the target neural tissue. The stimulation subsystem includes at least one "stimulator" for stimulating at least one brain region. An electrical stimulator may be at least one electrode having at least one contact for providing electrical stimulation. Using a multiplexer or other method, this contact can also be used for sensing electrical activity. When chemical, the stimulator may be at least one catheter having at least one distal tip from which at least one drug may be delivered to accomplish neuromodulation. A stimulator can be an electrical lead originating from a distant source which can provide current pulses or pulse trains, or can be a self-contained and self-powered local or remotely programmable integrated needle electrode/stimulator circuit, can be a catheter or a catheter/lead combination. Since any of these combinations can be used to stimulate target regions, specific embodiments can be understood to be interchangeable, as is known to those skilled in the art. Stimulators can be attached to, communicate with, provide power, and otherwise cooperate with sensors, and can transmit sensed data from the sensors back to the BND. The "modality" of modulation refers to the type of stimulation which occurs e.g., drug, optical, TMS, or electrical.

As used herein, the term "sensing subsystem" refers to all sensors and related circuitry related to sensing information related to at least one characteristic of sensed neural tissue. The sensing subsystem includes at least one sensor.

As used herein, the term "sensors" refers to one or more sensors which may be electrical, magnetic, chemical, metabolic, light, biosensor or any other sensor used for detecting, either directly or through a transformation, any activity, structure, metabolism, composition, process related to, or product of sensed neural tissue.

As used herein, the terms "target brain region", "neural target", and "target" all refer to a region of the brain which is an intended site for modulation.

As used herein, "sensed data" refers to data sensed from at least one or more electrical, chemical, optical, biosensor, or other type of relevant sensor. Sensed data can be sensed from implanted or external sensors, and instrumentation including functional neuroimaging devices.

As used herein, the term "result data" refers to results of processing and evaluation operations which can be performed on sensed data from implanted or external sensors and which may be used to guide or alter neuromodulation therapy.

As used herein, the term "database" refers to a quireiable information storage system used by the BMS. Such information can included population normative values or self-norm values related to sensed data, which can be values from prior sensing of the subject, path coefficients related to brain network models, linked rules used in performing stimulation.

Network Paradigms for Neuromodulation Treatment

The publication rate for studies exploring current and new techniques for neuromodulation of brain disorders is increasing steadily, as are the number of new clinical trials seeking to approve brain stimulation for the treatment of these disorders. Additionally, new methods and technologies are being developed as evidenced in numerous current patents and pending applications. The following are examples which generally describe methods and systems of neurostimulation for the treatment of various brain disorders which can be adapted to provide neurostimulation as described herein: U.S. Pat. Nos. 5,299,569, 5,470,846, 5,263,480, 5,540,734, 6,066,163, 6,061,449, and 6,539,263. While these prior art examples provide a number of useful advantages for treatment of various disorders, none provide such therapy using neurostimulation specifically designed for the treatment brain networks.

In the treatment of tremor, the therapy can be provided by disrupting activity, such as hyper-synchrony, in regions of the motor cortex. In the treatment of seizures, the therapy can be provided in order to disrupt the emergence of epileptiform activity, and stimulation can occur in an area where this increased synchrony was detected. In the treatment of some types of pain, treatment can be provided to block ascending signals so that these do not reach the areas of the brain which are responsible for the subjective sensation of pain (e.g. blocking ascending fibers of spinal or thalamo-cortical tracts). While treatment of these disorders may also benefit from network stimulation, sufficient relief can obviously occur when stimulation is designed with respect to stimulating a specific site, regardless of the state of the network in which it is a part. In contrast, psychiatric and other higher order disorders of consciousness certainly involve distributed brain networks, and relative activation as well as communication between different nodes of the network underlie various aspects of the disorder, and must be taken into account in order to provide improved treatment outcome.

The existence of brain networks, and methods for identifying the brain regions involved in these networks, is well known (e.g., Mcintosh & Lobaugh, 2004; Kong, et al., 2005). Evidence indicates that activation of one area is functionally significant in relation to the state of the rest of the network within which that activation takes place. The state of the network is likely just as important as the activation itself with respect to the functional role of that. In other words, the functional relevance of a brain area depends on the status of other connected areas i.e., the context within which the region is operating. As Mcintosh (2004) notes "A region can participate in several behaviors through variations in its interactions with other areas". Studies have explored the relationship of these networks to different brain disorders, including disorders of consciousness or with aging, and to loss of consciousness during anesthesia, and have demonstrated pathology in the primary networks of different disorders as well as the existence of putative compensatory networks (John, 2002; Prichep et al 2002; Stefurak et al, 2003; Mayberg, 2003; Mayberg et al. 2005; Peled, 2004; Gilliam, 2004; McIntyre, 2004; John and Prichep 2005; John 2005). However, while networks underlying both normal and pathological functioning, as well as networks related to different characteristics of various brain disorders, have been well documented, these have not been incorporated into the techniques used to create, or adjust, treatment methods in the emerging field of neuromodulation. The prior art, and current practice, approach stimulation of one or more regions as if these were isolated structures, and the operational principle is simply summation: if stimulation of one area is useful, two might even be more so. This strategy fails to utilize the growing understanding provided by studies of brain networks, which forms the basis of the methods of the current invention.

Evaluating and treating networks using neurostimulation is more promising than treating individual brain targets. Even when neuroimaging procedures indicate normal activity levels in regions of a brain network, the communication between two or more nodes of a network may be abnormal. This may be reflected by abnormal covariance (e.g., path coefficients) identified by network modeling of sensed data (e.g., McIntosh, 2004). Accordingly, therapeutic stimulation may strive not only to increase, decrease, normalize, positively/negatively reinforce, or otherwise modulate the relative activity of different regions of a path or network, but can also be designed to alter the interactions which normally exist between these regions. Network interactions may entail modulation of one area by another, which may be positive, negative or both, due to different fiber tracts or "paths" that join the regions of the brain network, and may also include reciprocal interactions. Modulations of one area by another may occur directly or may be mediated by at least one other intervening structure which may receive inputs from other regions of the network as well. In one embodiment, information is utilized about network interactions, and/or neuroanatomical connections, between different regions of the network in order to identify target structures, set the initial neuromodulation protocols, and guide the adjustment of neuromodulation protocols during treatment. Further, using the concepts of transfer entropy, the covariance between A & B can be quantitatively decomposed into the effects of A upon B, the effect of B upon A, and the "mutual information" reflecting the common action of some C upon both A & B (Friston et al, 1992, Imas et al, 2005). By using linking rules which adjust stimulation in one region to that provided in another, based upon, for example, models of networks the brain network can be treated rather than just treating isolated regions without adjusting stimulation in relation to the network.

Pending U.S. application Ser. No. 10/872,271, to Lozano et al. (the '271 application), describes a method of treating depression, mood disorders and anxiety disorders using neuromodulation. The '271 application describes treatment using stimulation to modulate "a predetermined site" which may be "a subcallosal area" that includes "subgenual cingulate area, subcallosal gyrus area, ventral/medial prefrontal cortex area, ventral/medial white matter, Brodmann areas such as 10, 24 or 25". These areas were chosen, in part, due to a number of neuroimaging studies previously performed by the inventors of the '271 application which showed that these areas were characterized by abnormally high metabolism in depressed patients. A portion of patient data included in the '271 application was also included in a study (Mayberg et al, 2005) which reported that neuromodulation via direct brain inhibitory stimulation of the Brodmann 25 area led to successful treatment in 4 of the 6 patients. Generally, the '271 patent teaches stimulating a pre-defined neural target which has been previously implicated in the disorder being treated, which in this case was depression. The '271 application further describes stimulation of several targets which have been linked with a depressive disorder. However, these targets are not recognized as being engaged in one or more networks which are associated with (e.g., which correlate with) the emergence of symptoms of depression. In the '271 application, one or more neural targets are stimulated independently without a consideration of: 1) the relative activity of one area in relation to other areas of a brain network, and 2) the influence that stimulation at one site may have on another. Unlike the current invention, the interactions or connectivity between two or more regions of the network, and the effects that stimulation of one target area may have on other target, or on non-target, areas of a network, are also not addressed. These omissions in the prior art are addressed by novel features of the methods and systems described herein, which thereby offer significant advantages over this art. Incorporating these network dynamics into the treatment methods is a main feature of the current invention.

Similarly, U.S. application Ser. No. 10/925,519 to Whitehurst, describes methods of treating a mood and/or anxiety disorder, by stimulating a series of structures, however these are identified by review of the relevant medical literature rather than by neuroimaging of the patients themselves. In any case, this prior art also does not discuss the existence or relevance of brain networks or the interactions which can occur between at least two brain structures that may affect each other by way of least afferent or efferent fibers.

Pending U.S. application Ser. No. 10/072,669, to Tcheng et al (the '669 application), teaches treatment of motor disorders via brain stimulation. While the '669 application notes that stimulation can be applied to "the GPi, thalamus, sub-thalamic nucleus, or any other structure of the basal ganglia (or elsewhere in the brain) that provides relief" it does not discuss stimulating more than one neural target, or neuromodulation of one or more networks in which the target brain region is involved. In contrast, it is stated that "the functional relationships among various brain structures are generally not very well understood, and" should not be used as "a definitive guide to brain activity involved in movement". In this prior art, neurostimulation simply occurs in response to sensed events, and the process for choosing, the structure, or structures, to be stimulated is not described. Further, there is no mention of treating a disorder by stimulating two or more neural regions of a brain network underlying the disorder.

The prior art does not describe tying stimulation parameters used in a first region to those used to stimulate at least one other region of a brain network underlying a disorder. The prior art does not describe tying (i.e. contingently adjusting) stimulation protocols used in a first region to data sensed in any other regions of a brain network underlying a disorder. The prior art does not describe contingently adjusting stimulation protocols used in a first region to data sensed in at least two other regions of a brain network, which are modulated by stimulation of the first region, at least one of which underlies a symptom of a disorder. A well known network that would benefit greatly by this linking strategy are the A9 and A10 structures of the dopamine system, wherein therapy intended to differentially modulate treatment of psychiatric disorders or movement disorders, may co-occur with dysregulation of the other structure and manifestation of unwanted symptoms. Lastly, while the prior art also teaches utilizing implantable neuromodulation devices having several leads, each of which may be placed in a different brain region (e.g., U.S. Pat. No. 6,066,163), it does not describe using these multiple leads to modulate two or more brain regions involved in a pre-defined brain network which has been associated with some characteristic of a brain disorder.

Two objectives of brain stimulation are particularly important with respect to network stimulation methods. The first relates to the endogenous adaptation/compensation which undoubtedly occurs during pathological development of a patient's brain, and may underlie some brain disorders. Adaptive changes between two or more nodes of a relevant brain network may be central to treatment, and treatment refractoriness, of different disorders (Peled, 2004). While the prior art addresses the issue of adaptation and compensatory modulations of endogenous activity in response to brain modulation, this issue is not addressed in relation to networks. Instead, the issue of adaptation to neurostimulation is discussed in relation to local phenomena, with respect to the specific region being stimulated (e.g. U.S. Pat. No. 6,665, 562, U.S. application Ser. No. 10/044,405 to Stypulkowski). However, since networks consist of multiple brain areas and the relationships among these areas, influencing one area of a network can lead to adaptation or compensatory responses in other areas of the network (e.g., Eytan, 2003). Accordingly, in line with the current invention, stimulation in more than one region of a network will assist in treatment by compensating for adaptation which may occur in a region of the network. Further, stimulation may be applied to different neural targets within a network in order to decrease the risk of adaptation that may occur when a single area is chronically stimulated over time. The prior art does not describe protocols which alternate stimulation across brain regions of a network to avoid adaptation of the network to stimulation, or describe adjusting stimulation of one area of a brain network based upon the endogenous or modulated activity of a different area of the network.

The second is treatment selection. Since different brain networks have been shown to be predictive of drug response with respect to drug type, independent of similar overt behavioral and mood characteristics, detection of pathological networks can determine two or more target areas for which NBN may be most effective. Imaging data derived from, for example, PET or scalp electrodes have shown to reflect network activity that accurately predicts response to treatment (John, 1994; Seminowicz, 2004). Accordingly, in line with the current invention, two or more neural targets can be selected for treatment based upon analysis of imaging data, for example characteristics of modeled brain networks of a patient suffering from a brain disorder. Further, the stimulation protocols can be chosen based upon the characteristics of two or more regions of the network, determined from sensed data which is analyzed using a network model or other appropriate methods. Additionally, parameters and brain targets can be chosen based upon the similarity of a new patient's brain activity, and brain network model, with those of previous patients who have been successfully treated with certain protocols. Having described the general goals of the systems and methods of the invention, specific embodiments will now be described in an enabling fashion.
Neuromodulation System Embodiments.

FIGS. 1a, 1b and 1c illustrate examples of brain neuromodulation devices 10a-c, which can be used to provide neuromodulation of brain networks in the treatment of various brain disorders. Considerable pending and prior art describing implantable neuro stimulation and drug delivery systems share features of the BND, and are commonly known by those skilled in the art. For example, U.S. 20030149457 contains a neurostimulation device which could be utilized to achieve neuromodulation of a brain network. It contains a stimulation subsystem having both electrodes for providing electrical neuromodulation according to a stimulation protocol and also a drug dispenser for providing pharmaceutical stimulation. It contains a computer subsystem with memory, a CPU, a real-time clock, communication subsystem for communicating with external equipment such as a patient programmer via, for example, telemetry, and a power supply. The computer subsystem also contains circuitry to perform signal processing and statistics on the sensed data in order to guide therapy. Its components operate to provide sensing from implanted sensors and processing of the sensed data to deliver either electrical or pharmaceutical treatment. Other examples of implantable neurostimulators are U.S. Pat. Nos. 6,066,163; 6,597,954, 6,051,017; 6,735,474; 6,735,475; and US application Nos. 20030204226, 20030135248, all of which could be utilized to provide modulation of brain networks by adjusting their treatment programs so that they occur according to the methods of the present invention.

FIG. 1a shows an embodiment of the invention where an implantable BND 10a is an electrical deep brain stimulator such as the Aptiva™ produced by Medtronic. The device 10a has a connector component 12a to which one or more leads 14a, 14b can be connected. The leads 14a, 14b each have one or more electrical contacts 18a, 18b which are placed to stimulate the target areas of the brain network according to stimulation protocols. The contacts 18a, 18b can also serve as sensors which sense the endogenous electrical potentials. The control subsystem 34 can permit some contacts 18a to sense data from target brain regions while other contacts, 18b simultaneously stimulate target brain regions. For example, using a multiplexer, each of the electrode contacts can be operationally connected to a stimulation subsystem or a sensing subsystem of the device 10a. Although the leads 14a, 14b each contain at least one electrode contact, preferably a plurality of independently operable electrode contacts are provided.

FIG. 1b shows an alternative embodiment, where an implantable BND 10b is a drug pump containing at least one drug to be dispensed during neuromodulation treatment. The device 10b has a connector component 12b to which one or more catheters 16a, 16b can be removably, or permanently, connected. Each catheter tip is implanted to deliver drug to a target brain region which is part of at least one brain network. The catheters 16a, 16b may also have at least one distal component 20 which is electrically connected to the device 10b, so that, in this embodiment, the stimulator provides both electrical and chemical neuromodulation. The distal component 20 can be an electrical contact to provide electrical sensing/stimulation of the target, so that the device 10b can provide both electrical and drug neuromodulation. The distal component 20 can be an optical sensor or stimulator to provide optical sensing/stimulation for the target, so that the device 10b can utilize optical neuromodulation and optical sensing. The distal component 20 may also be at least one chemical sensor, optical sensor, electrical sensor, biosensor, or other sensor for sensing a characteristic of the target area. The distal component 20, may also be a valve which is controlled by the control subsystem 34 in order to control release of drug, or the valves may be located more proximally, for example, the connector component 12b can contain a programmable valve structure. The treatment program of the control subsystem can instruct for the operation of these valves to provide differential pharmacological modulation of the target brain regions of the brain network according to stimulation protocols of the neuromodulation device 10b. In most embodiments, the BMS utilizes one or more implantable drug delivery devices which have active components for controlling, for example, rate, amount, and type of drug to be delivered as part of therapy. However, passive drug pumps can also be used. If passive pumps are used, then the drug delivery parameters may be set independently, but according to linking rules, to provide drugs to two or more targets in the treatment of the brain network. Lastly, passive pumps can be used with active accessories (e.g., U.S. Pat. No. 6,880,564 entitled "Dosage control apparatus"), which can be used to control the rate and location of drug delivery within the network being treated.

FIG. 1c illustrates yet a further embodiment of the invention where an implantable brain neuromodulation device 10c is an electrical deep brain stimulator having a connector component 12c to which only one electrode lead 14c is connected. The lead 14c has two series of electrical contacts 18c, 18b to stimulate the first and second target brain regions of the brain network according to neurostimulation protocols of the BND 10c. For example, a brain structure may be stimulated by 18c and its efferents may be stimulated by 18d, in order to desynchronize their firing, so that stimulation of this structure can occur without resulting in unintentional modulation of a second brain region in another part of the network. Similar to 18a and 18b, the series of contacts 18c, 18d can also serve as sensors.

Figure 4:
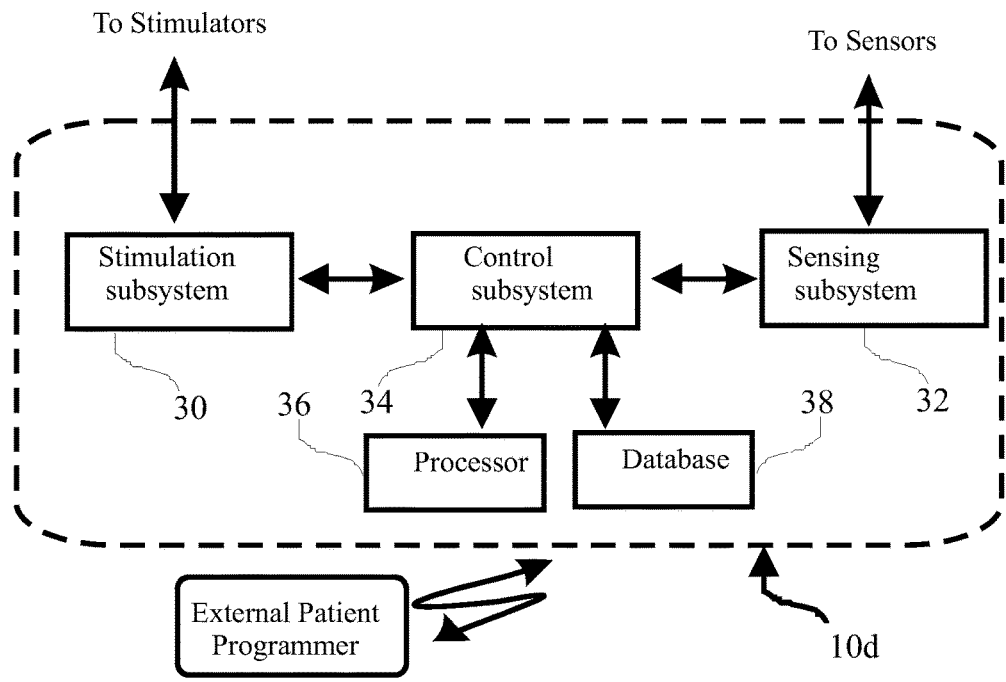
FIG. 4 shows the components of neuromodulation system which can provide neuromodulation of a brain network.

FIG. 4 illustrates the functional components of the BND 10d which includes a sensing subsystem 32 which controls sensing operations and communicates with sensors, a stimulation subsystem 30 which controls stimulating operations and communicates with stimulators, and a control subsystem 34, which communicates with and controls the sensing subsystem 32 and the stimulation subsystem 30. When the BND 10d, provides drug therapy the stimulation subsystem 30 contains an active or passive mechanism for biasing the flow of a drug contained in a reservoir so that it is dispensed approximately in an intended manner. The control subsystem 34 contains a rechargeable power source, processor, memory, real-time clock, and communication means to achieve the control processes provided for in implantable BMDs as are well known and described within the cited prior art. The processor 36 may be realized as a computer subsystem with processing circuitry which resides within the controller subsystem and which communicates with the sensing and/or stimulation subsystems. Such communication may be accomplished by means of an information transmission system which includes telemetry means. The processor can processes sensed data to produce result data, which is then used to determine if, and what type of, neuromodulation is needed. The computer subsystem also contains hardware for processing the sensed data by at least filtering, amplification/attenuation, A/D transformation, correlation, modeling, signal processing, and registration. The computer subsystem also permits the BMS to initiate or modify neuromodulation based upon for example, predefined protocols, user input from an external controller, sensed data, result data, or time of a real-time clock. The BMS can communicate with the processors 36 of one or more implanted BNDs to coordinate neuromodulation of brain networks. It should be noted that in conceivable circumstances, such as a multi-bed intensive care unit or coma ward, there might be a central station that remotely communicates with the processors of multiple BNDs which are treating multiple patients.

A processor 36, which can be provided with programmable code, or circuitry for achieving the functions of this code, provides the treatment program of the BND 10*d* with the ability to evaluate the sensed data using signal processing algorithms and/or modeling, and to compare the sensed data to treatment criteria. Treatment criteria define normal or desirable values and ranges for the sensed data. When sensed data meet treatment criteria (e.g., restore abnormal values to desired levels such as within a normative range), then the criteria being evaluated, for those region(s) of the brain network being evaluated, are met. Often, when criteria are met the modulation parameters are not changed. When the sensed data fail to meet treatment criteria, then stimulation must usually be either initiated or adjusted. Alternatively, the treatment protocol may dictate that a treatment criterion must fail to be met a number of times, or for a specified duration, or to a specified degree, before the evaluation protocol defines the treatment criterion as not being met. This may occur by storing a history of comparison results, sensed data, or summaries of sensed data in the database 38, and the control subsystem 34 can evaluate this history, for example, by comparing it to treatment criteria related to number of events or duration of the events, self-norms or trends. The treatment program can contain a control protocol which directs the control subsystem to control the treatment according to whether the treatment criteria are met or not, in relation to linked rules. For example, the criteria can require that data sensed from two nodes of a network each meet specified criteria, which may be set in relation to each other. The treatment criteria can be selected by the control subsystem 34 from the database 38. The database 38 can store values related to the sensed data and can contain self-norms, population norms, linking rules, and other information and reference values utilized by the control subsystem during the sensing, stimulation, and evaluation processes carried out to provide the intended neuromodulation of the brain network. The historical records of sensed data itself and transformations and summaries of the sensed data, can also be kept in the database of the BMS. The database can store normative values of, for example, relative activity levels between structures. The database can also store stimulation protocols, including protocols to deter adaptation by the network to treatment stimulation which include, alternating different parts of the network. Adaptation-related stimulation protocols can be specifically triggered when adaptation, such as network adaptation, is detected by the BMS.

Figure 5:
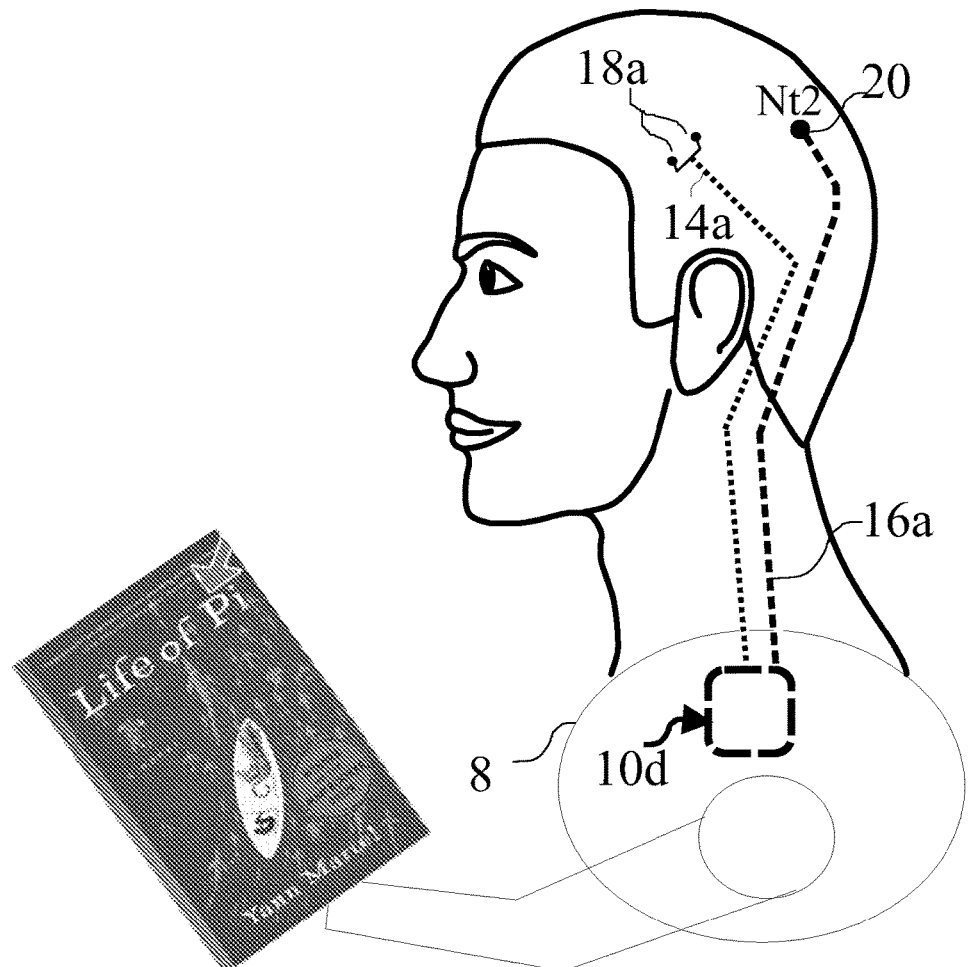
FIG. 5 shows an implanted neuromodulation system, with stimulators situated to provide neuromodulation of a brain network.

FIG. 5 shows an embodiment of the BMS where a BND 10*d* is implanted in a patient in order to provide stimulation to two regions of a brain network underlying a disorder. In this embodiment the BND 10*d* has a lead 14*a* which has a set of two electrical contacts 18*a* which provide electrical stimulation to a first neural target Nt1, and a catheter 16*a*, which provides drug modulation of second neural target Nt2. The electrical contacts 18*a*, and the distal component 20 of the catheter can provide both electrical stimulation and sensing.

Methods for Neuromodulation of Brain Networks.

FIG. 2A illustrates an example of a method for neuromodulation of brain networks in the treatment of brain disorders. First, a patient is identified 100 as having a brain disorder and also as appropriate for treatment. One or more candidate brain networks which are related to the unwanted symptoms of the disorder are then identified 102 from neuroimaging data. The BND is implanted 104 so that at least one brain network may be stimulated. Modulation of the brain network 106 then occurs in the treatment of the brain disorder. For example, stimulation may occur in two regions in order to compensate for interactions between those regions, and this can occur using linked stimulation rules as will be discussed. In the next step, the effects of the treatment provided by the modulation of the brain network are evaluated 108, and either modulation is then repeated 106 without adjusting the parameters, or modulation parameters are adjusted 110, and then modulation 106 again occurs. When neuroimaging data is obtained and treatment is evaluated 108 the data can be compared to reference data using treatment criteria. This comparison may result in either a positive result wherein modulation parameters are adjusted 110, or a negative result wherein modulation parameters are not adjusted, and then stimulation is repeated 106. Alternatively, evaluation of the treatment is not necessary on a regular basis, and neuromodulation treatment simply consists of steps 100 to 106, wherein modulation of at least two areas of a brain network occurs using a stimulation protocol which utilizes linking rules.

With respect to patient identification 100, appropriate patient identification may be based upon a number of criteria selected by the medical experts providing treatment. For example, patients who have been refractory to various medications over a sustained period are obviously prime candidates, as are patients who suffer disorders for which medication is not helpful (e.g., traumatic brain injury). Patients can be selected based upon medical history, psychological or neuropsychological testing, neuroimaging data collected from internal sensors such as acutely implanted electrodes, or external sensors, such as the results of structural, and/or functional neuroimaging tests. Patients who demonstrate certain profiles of test results can be compared to profiles of previous patients who either did, or did not, respond well to neuromodulation treatment. In the latter case, the candidate patient may not be selected as appropriate for therapy.

With respect to identification of brain networks 102 which will be modulated during treatment, in one embodiment, sensed regions, target regions and neuromodulation parameters for treatment may be chosen either based upon the knowledge gained from the patient or from population data. The data can include models of the putative brain networks responsible for a particular brain disorder and appropriate targets of the network can be identified prior to surgery. A comparison of a model of the patient's brain networks to models of networks of prior patients for whom treatment was successful can assist in designing the therapy, including selecting treatment sites for sensing and stimulation according to the similarity of a patient's profile with profiles of past patients. For example, in one NBN treatment method a patient can be classified into one of a number of existing sub-groups using discriminant or cluster analysis of measures of the network, or transformed measures (e.g., z-transformed, factor scores, model coefficients). Generally, this method includes the steps of obtaining test results such as neuroimaging data for a patient, making a comparison of the test results of the current patient to past test results of patients who were successfully treated using a particular neuromodulation treatment protocol, classifying the current patient based upon this comparison, selecting a treatment paradigm based upon this classification. Additionally, the one or more targets of a brain network which are chosen for treatment may include structures which have been shown to have functional or structure interaction, for example, due to afferent or efferent pathways which connect the two or more structures, either directly or via at least one intermediary structure, and which are related to the pathological condition. Further, sensed/target regions and neuromodulation protocols may be chosen based upon imaging of a subject's brain, using some of the examples related to identification of brain networks which are provided in the section entitled identification of brain networks.

In steps 100 through 108, functional imaging data may used to identify and evaluate the brain networks of a patient before and during treatment. Although the BND can sense data and evaluates this data to guide treatment, the steps of the method of FIG. 2A can occur in a non-automatic fashion under the direction of a physician. During any of the steps of the method, neuroimaging data can be obtained for a subject during one or more conditions including, baseline conditions, (for example, during rest eyes-open, during rest eyes-closed), or during activation while engaged in at least an emotional task, a sensory task, a memory task, a stressor task, cognitive task, target detection task or other type of task which may activate the brain network underlying a characteristic of the brain disorder, or by comparing the resting and activated states. Imaging data may also be obtained for a subject while the subject is presented with stimuli to which a response may, or may not, be required, or using stimuli which have a low or high emotional aspect (e.g., faces with different expressions, unpleasant or disturbing images), or during activation with cues related to a disorder, such as displaying drug paraphernalia to a person with substance abuse disorder or phobic objects to one with a phobia. Subjects may also be asked to internally generate stimuli (e.g., think of an unpleasant experience). Imaging data may also be collected while the patient is exposed to a treatment medication, a substance which may acutely modify or worsen the brain disorder, or a substance which will alter brain activity or metabolism in a useful manner with respect to gaining information about the brain network underlying a characteristic of the disorder. Imaging data across conditions can be manipulated (e.g., subtracting a baseline condition from a task condition), processed, and analyzed using numerous techniques described in the literature. The results can then be used to obtain information related to the brain networks, can be used to assist in determining the placement of the sensors and stimulators, and can be used to adjust both initial as well as subsequent parameters for neuromodulation.

Generally, by measuring the amount of abnormal activity, functional imaging data can be used to quantify the disease state and changes in this state that occur during the treatment of the disorder. Rather than occurring within the BND itself, under the direction of a physician, abnormal activity in dispersed portions of a network may be measured in a number of manners, for example, by superposition of three dimensional source localization of the generators of quantitative EEG (QEEG) measurements. The characteristics of sources waveforms (e.g., coherence, band-limited power) can be referenced to either population or "self-norms". By "self-norms" is meant a set of parameters derived from a reference state of the patient, for example, prior to the onset of a BMS intervention. A number of well performing QEEG source localization methods are currently available such as, for instance, Low Resolution Electromagnetic Tomographic Analysis, also known as LORETA (Pascal-Marqui et al). The sources may be constrained by either MRI's previously obtained from the individual patient or slices from a Probabilistic MRI atlas such as that provided by Evans et al. The use of QEEG imaging provides the advantage of confirmed normative data for regional brain electrical activity which is not yet available for other neuroimaging methods. The current sensed data can occur interleaved with intervals of brain stimulation in order to avoid the issue of electrical artifact with respect to evaluation of sensed data, especially when the neurostimulation occurs in a frequency range that is within the bands of power being measured.

Using data about one or more brain networks of the patient and some aspect of the patient's disorder, the relationship between these can be established by imaging techniques such as path/PLS analysis and SEM or transfer entropy computations. Targets for neurostimulation, and candidate neurostimulation parameters, can be determined due to aspects of the model analyzed using methods such as correlation of hyper- (or hypo-) activation with some aspect of the disorder, absolute or relative activation, connectivity (path) coefficients, directionality of influences within a network, latency differences between activation of different regions, etc. Alternatively, locations for neurostimulation and the initial stimulation parameters can be determined by any other criteria, such as a neurosurgeon's experience, neuropsychological tests, or other means.

With respect to implantation of brain modulation system 104, either frame or frameless techniques may be used to ensure that stimulators are implanted correctly to modulate the intended targets. As is well known, if frameless techniques are used, then the imaging data is used to make a 3-dimensional virtual map which is fit to the stereotaxic frame of reference in the surgical field using reference points located on the patient's skull. There are many instruments for frameless image-guided surgery which can assist the neurosurgeon in determining accurate placement of the neuromodulation leads and/or catheters with respect to the intended neural targets (e.g., Stryker Navigation Neuro Module). In one embodiment of the method, if a stimulation electrode is configured as in FIG. 1c, then one section e.g., 18c, can be implanted to stimulate a first target area of a brain network, and a second section e.g., 18d can be situated in a nearby structure or an afferent or efferent fiber tract, so that the target structure can be stimulated in one manner, while its projections are stimulated in another manner. For example, if the activity of the target region is to be stimulated in an inhibitory fashion, but the afferent pathway leads to a structure which should not be affected, then the second section 18d can be stimulated in a fashion that disrupts, blocks or otherwise counteracts the effects of the signals which would normally travel along that pathway thereby creating a functional lesion that can be reversible or intermittent if such might be advantageous. Step 104, can consist simply of implanting at least 2 stimulators in a brain network In one method of providing NBN treatment the neurosurgical procedure for implantation of brain modulation system 104 occurs as follows. First at least a first sensor or stimulation electrode is placed in one neural target of a brain network and a second sensor or stimulation electrode is place in a second neural target of a brain network. Secondly, different stimulation protocols can be evaluated in order to determine the effects of the neuromodulation on the network. Thirdly, locations are chosen which produced not only the intended stimulation of target structures, but also either beneficial interactions between structures or interactions which could be countered by stimulation using linking rules. The evaluation of neuromodulation protocols and sites of stimulation can be accomplished with the active participation of the patient, whereby the patient provides self-reports for different mood, cognitive, or behavioral rating scales. The patient may also be given drugs or exposed to stimuli which cause changes in the target brain network that are informative about the efficacy of the neuromodulation treatment. If a model of the brain network has been generated for this patient, and the model dictates that certain amounts or types of activity should occur in different regions in order to provide treatment, then the stimulation protocol, including sites of stimulation, may be changed until these target values are evidenced by sensed data.

In FIGS. 2A, 2H, 2I, and 2J, the step of implanting can rely on steps which evaluate the brain network using the principles that have been disclosed herein. The stimulation protocol used during implantation, including a location used at stimulating one or more sites, may be considered as an early part of the treatment protocol. A change in implantation site, or using one candidate lead location within a selected subset, may be considered a characteristic or parameter of the treatment protocol. In one embodiment, shown in FIG. 6, a method of providing treatment for a brain disorder begins with the implantation of two electrodes and the determination of where at least one of these should be located.

The electrodes (or other sensors or stimulators such as a drug infusion pump that can be used to provide drug to a patient) can be controlled by a computer system configured with circuitry for operating the electrodes that are used during implantation and also, in some methods, relied upon for subsequent treatment. Such a computer system, used in combination with related circuitry and software, is described in US2010/0057159 to Lozano, filed Apr. 30, 2009, which is incorporated by reference herein. As is generally known, a computer system for assisting with implantation can be supplied with stimulus generator circuitry, sensing circuitry, signal processing capabilities for sensing, amplifying, conditioning, and analyzing the signals that are sensed from the patient's brain. The software is configured to run the hardware and to provide customized routines related to implantation steps of FIG. 6. The software can also allow the recorded signals to be compared to a database, or evaluated in numerous manners in order to evaluate the data (e.g., brain activity features) that are measured during the protocols and conditions that occur during implantation. Additionally, an implantable brain modulation device may be controlled by the computer system during implantation, and this can be realized as a physician programmer or external patient programmer.

In one embodiment, the external patient programmer of FIG. 4 can serve as the computer system and can accomplish, or assist with accomplishing, the steps of the implantation method. In this case the external patient programmer contains circuitry and means for providing the operations required during implant, including providing communication with and control of an implantable brain modulation device. The computer system/external controller is configured to sense from and/or stimulate the brain in programmable manners to achieve the operations of the implantation procedure. While this may be achieved in part using the implantable device, this approach may be selectively avoided due to restrictions in the function of the implanted device. For example, this may be avoided in order to save battery power of the implantable device and also to provide stimulation, sensing, and analysis capabilities that are not easily implemented using an implantable device due to such factors as restricted memory and communication between the implantable device and the computer system.

While the operations used during implantation can involve mostly automatic, closed-loop routines implemented by the computer system, semi-automatic or manual methods can also be provide whereby the surgeon manually changes stimulation protocol parameters using the software of the computer system. As is well known, implantation usually occurs after patients have been selected due to inclusion criteria that suggest the patient is an appropriate treatment candidate. Identification/evaluation of a brain network targeted for treatment can also occur prior to implantation, as shown in steps 100 and 102 of FIG. 2a.

Figure 6:
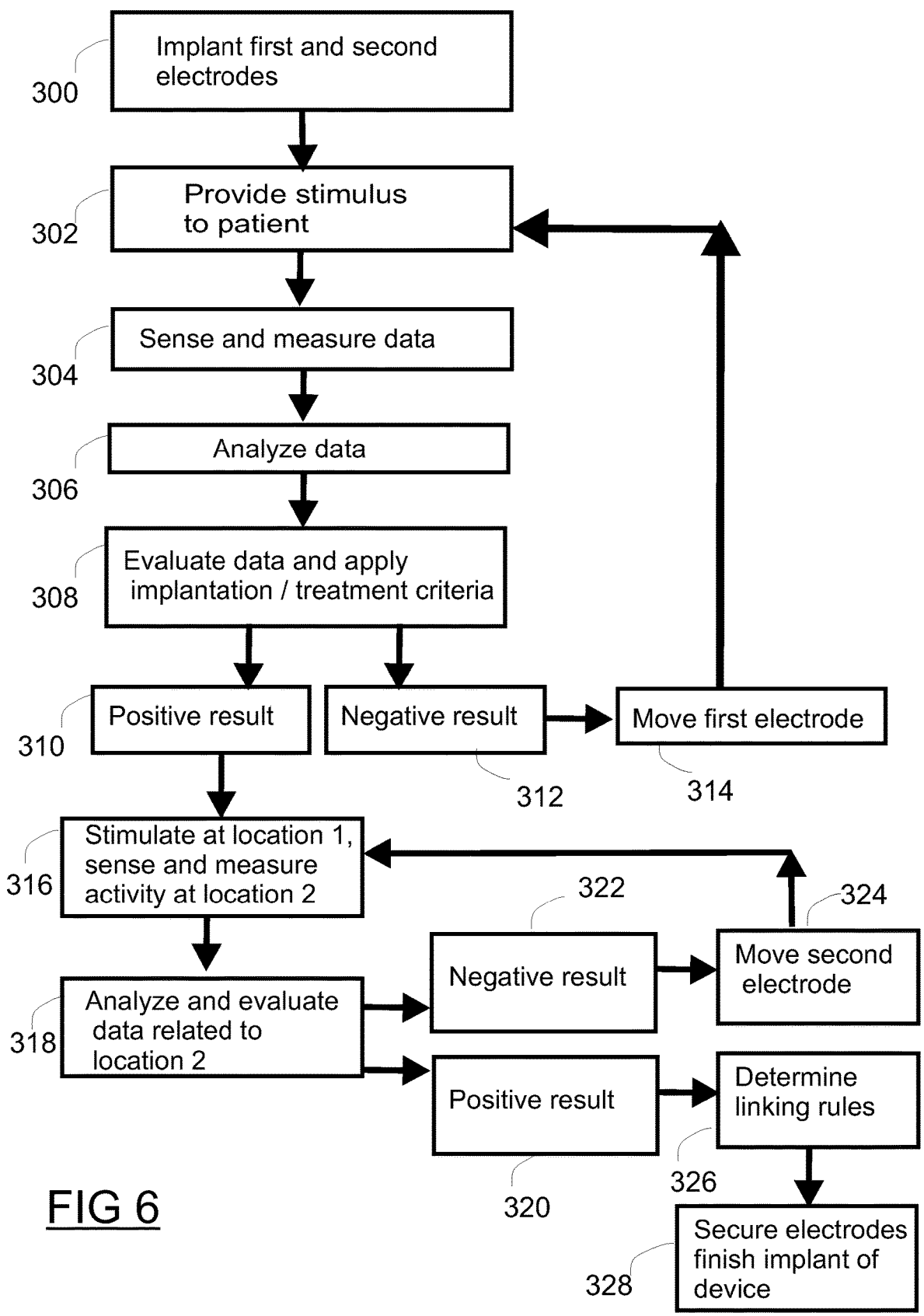
FIG. 6 shows a method of providing treatment for a brain disorder including implantation of two electrodes and the determination of where at least one of these should be located.

In one preferred embodiment of evaluating and selecting locations for electrodes during implantation, the method starts with step 300 of FIG. 6 in which a first electrode is implanted in a candidate location of a first brain region of a brain network and a second electrode is implanted in a candidate location of a second brain region of the brain network. The two brain regions may be adjacent nuclei of the same brain structure, or may be distal, where the second brain structure receives, or is believed to receive, afferent input from the first, or vice-versa, as may occur through a fiber pathway. The initial locations used in step 300 may be selected based upon a putative neural network, which can be evidenced using imaging means such as PET, prior to surgery. Other means may also be used to more specifically select locations, for example, the electrode position can be moved while searching for a particular type of neuronal activity (or other sensed data) to be sensed from the electrode. This can occur with steps 300 to 314, excluding step 302. As evidenced in FIG. 6, this activity (e.g., spike patterns, frequencies of discharge, etc,) is known to be a signature of the neuronal populations that reside within an intended target of the brain region in which the electrode is to be implanted. The electrode locations can be selected in part by ensuring that a particular type of activity occurs at the candidate locations, while if this does not occur, then at least one location for an electrode can be changed, until the desired activity occurs. The activity which indicates an appropriate target area has been located can be activity that is sensed from the electrode at the location during rest, or in response to a stimulus such as may occur when the patient is instructed to do a task so that data is collected, at least in part, during mental load or during an emotional task. The stimulus can also be stimulation provided at the location of the electrode being evaluated or at a different location.

Evaluating and selecting at least one location in a brain region of a brain network for stimulation can comprise, providing to the patient a stimulus 302 that is intended to alter neuronal activity in at least a first brain region of the network. This stimulus can be an electrical stimulus provide by one of the electrodes, or a stimulus such as an emotional task which may include showing the patient emotionally oriented pictures or videos to which the patient may respond or for which a patient may simply view. The provision of the stimulus to the patient may not be continuous and may be provided periodically, with intervals between individual stimuli, in an "on-off-on" fashion. Further, the stimulus can be a cognitive task or a behavioral task and may include having the patient imagine various scenarios which may be positive, neutral, negative, with high or low emotional content/valence.

It is well known, from neuroimaging studies that certain brain regions will respond preferentially to different types of emotional stimuli, and so differential activation of a brain region in response to the stimuli can be used to select appropriate target electrode locations. In step 304, sensing and measuring data occurs. In this step, rather than, or in addition to, sensing and measuring neuronal activity, behavior of the patient may be recorded and/or measured. For example, the patient may be asked to respond to the stimulus, by providing information about an emotional state or the content of a thought or memory. Alternatively features of sensed data such as magnitude of a particular frequency of firing of neurons recorded from the electrode, or firing rate or particular pattern can be measured. The sensing and measuring of data from the subject can occur prior to, during, and after the provision of the stimulus. These operations can also occur during other steps of this method as will be described.

The sensed/measured data are then analyzed 306 and relevant features are extracted and stored in computer memory as reference values if appropriate. The sensed data can be evaluated 308 by comparing the data related to the presentation of the stimulus, with data related to intervals when the stimulus was not provided to the patient (i.e., "baseline" or "stimulus off" data). The "stimulus-on"-sensed activity can be compared to the stimulus-off activity, for a particular structure, or in relation to the activity of a first brain region to a second brain region. This may occur in many manners which has been described herein in order to assess stimulus-related changes and determine if these changes meet target implantation criteria related to the amount or type of change that is defined. The step of evaluating the data 308 can include determining if the neuronal activity related to the stimulus is at least a target amount or type of activity, either in an absolute sense or relative to a reference value. The change evaluated by implantation criteria can include, for example, activation of the first brain region relative to the second brain region, can be is assessed in relation to the activation of these regions during a baseline period. This can be extended to any measurement of network interaction, such as the correlation of at least one feature calculated from the sensed activity of the first and second brain regions, and this correlation can be compared to the correlation that existed during a baseline period or to a reference level of correlation. The target amount or type of activity can be defined by the activity related to the stimulus causing specified change in relation to the stimulus-off activity as defined by treatment criteria, which here serve as implantation criteria. For example, the stimulus should evoke a change in activity of at least a certain amount relative to baseline pre-stimulus sensed activity, or should create a change in the relative activation levels between the first electrode and second electrode. The change, and criteria used to evaluate the change, can also be related to different types of interaction such as correlation between brain regions in which the electrodes are placed. If the target result occurs (i.e. a criterion is met) then this can serve to identify the candidate location of the first brain region as one for which the provision of neuromodulation treatment should be efficacious. This positive result 310 can indicate that the location of the electrode should be kept and this can be selected as approximately the location which will be permanently used during treatment (at least designated as one of a set of permanent locations which are promising) since the activity related to the stimulus is at least a target amount or type of activity. In the case of a negative result 312, then selecting a different location for implanting the electrode may occur 314 and the prior steps 302-308 can be repeated until the target amount or type of activity occurs. In this manner the selected electrode locations will meet implantation criteria designed to insure certain activity, or a change in activity, can be evidenced at that location.

In a further implementation of FIG. 6, which is a variant on steps 300 to 314, stimulation of a first brain region as provided in step 302 can be evaluated as effective when data collected from multiple locations (steps 304-306, where sensing is applied to location 2 and additional locations as well) evidence that these other locations (e.g., downstream structures) are modulated so that these do not respond to the certain stimuli (e.g., sad stimuli) compared to how these respond to the stimuli when the first region is not stimulated. In this manner, a location for the first electrode which modulates the network can be preferentially selected to be a permanent location. In other words, a decrement in the change of activity which an emotional stimulus evokes, as sensed across multiple structures of a network, which is found when providing a stimulus to a location of a first target structure 302, can be seen as successful treatment of a brain network. This can serve target amount or type of activity that is defined as at least one of a set of implantation criteria that is used in step 308. This method of evaluating and selecting lead locations can be used in the weeks or months that follow the implantation procedure as well. In this case electrode 1 is moved functionally, rather than physically, by selecting a different treatment protocol or lead location in step 314 at which stimulation is provided. The steps 304-312 can be accomplished using various neuroimaging techniques (e.g. PET) in order to evaluate not only the activity at a first location, but also multiple other locations. In this manner, lead locations which produce the desired effects on multiple regions of the network, and cause these to meet treatment criteria, can be preferentially selected for use during treatment. As such, the modulation of the entire network and the type of amount of activity recorded across multiple brain regions can be used as a target to which treatment criteria are applied.

Although steps 300 to 314 may themselves serve as the entire method of implantation, additional steps can further improve the implantation method. In the case where at least one location is found to produce a positive result, then stimulating at that location and evaluating other sites 316 can occur in order to see what affect this has on other regions of the network (e.g., downstream or other brain regions that are modulated by changes in activity of the first brain region). It may be desirable to select a site at the first brain region which also is able to modulate, or not modulate a secondary region. For example, as discussed, in order to more fully modulate the network it may be desirable to indirectly stimulate at least one other structure in order to more fully modulate the network. An electrode location at which stimulation achieves this effect may be selected over others that do not. In contrast, certain downstream structures may wish to be avoided since indirection modulation of these regions produces unwanted side effects such as particular undesirable symptoms. In this case the location which will be selected to be permanent can be changed with other sites that have met prior target implantation criteria, until one his found that has less unwanted indirect stimulation as evidenced by activity sensed from these other structures. Accordingly, this further shows that secondary brain region stimulation can be included as part of the target type or amount of activity that is assessed, and compared to implantation criteria, in the processes of selecting a location for the first electrode, in order to provide improved modulation of a brain network.

Proceeding forward from Step 314, identifying a location in the second brain region occurs at least in part by electrically stimulating the location in the first brain region with at least one stimulation protocol 316, and sensing, analyzing and evaluating sensed data from the second location 318, in order to determine whether a stimulation induced change in the activity of the second brain region occurs in response to this electrical stimulation (in this case positive result 320). The change may produce beneficial interactions between the first brain region and the second brain region such as increased activity at both, where the second brain region is desirably regulated by stimulation in the first brain region. Further, in the case where the stimulation produces desirable changes in the second region, then during treatment, the second electrode may be used as a sensing electrode by the implanted brain modulation device in order to measure these indirect effects of stimulation. In this case, if these do not meet a treatment criteria then the stimulation protocol can be changed, at least once, in an attempt to cause these secondary effects to occur. Alternatively, the change may produce unwanted interactions which could be compensated for by stimulation of the second region. In this case the second electrode can be used as a sensor in order to monitor these unwanted effects of indirect stimulation and to enable the device to select a different protocol to cause these to be diminished or to provide compensatory stimulation to decrease side effects.

If the change does not occur 322 (negative result in this case), although it is expected, then the second electrode may be in the wrong location and is failing to accurately detect the effect of stimulation of the first brain region on other parts of the brain network. In this case the second electrode may be moved 324. Steps 316-318 can then be repeated until implantation criteria are met.

It is important to note that the information obtained during the implantation procedure (or when providing these steps during treatment), with respect to the indirect influence that stimulating in one brain area has on another, may be used to determine linking rules 326, or at least the initial linking rules used during treatment. This step may also utilize data collected during additional steps of stimulation. For example, stimulation can be provided at the second brain region to see how this modulates activity at the first region, and this reciprocal stimulation can be used to calculate appropriate linking rules. Alternatively, stimulation can be provided at the first region, and compensatory stimulation can be provided at the second region, and the compensatory stimulation can be evaluated, for example, by asking the patient to report on their mood, or other attribute that might be related to the side effect of stimulating the second region indirectly from stimulating the first region, using at least one stimulation protocol. The values of the stimulation at the second region can be adjusted until the desired effects are sensed/measured. Patient participation during this method can help to ensure that modulation of the network during treatment utilizes linking rules that adequately modulate the network effectively.

After the final electrode locations have been chosen the electrodes are affixed to their permanent locations and a brain neuromodulation device configured for operating upon the two electrodes is implanted 328. The provision of therapy to the brain network then occurs by stimulating (and also sensing when this is provided) with the brain neuromodulation device.

The method of providing treatment for a brain disorder can include an method for selecting sites for the electrodes in which a target amount or type of activity which identifies the brain region within the target area as one for which the provision of neuromodulation treatment should be efficacious includes producing at least a desired (e.g., relatively large) change in the activity of the first target brain region of a target network and relatively less change in the second target brain region. In this manner, changes in the activity of the second target brain region, which is an undesired side-effect, can be beneficially avoided.

Accordingly, in one embodiment of the method of FIG. 6, steps 300 to 314 are accomplished in which, during step 302, providing a stimulus to the patient includes neuromodulation at location of the first electrode and measuring indirect, induced activity at the location of the second electrode. In this case, if the measured activity at the second electrode indicates that stimulation at the first electrode does not produce modulation of the second, then the location of the first electrode is moved, functionally or spatially, because it does not produce the wanted changes in the second electrode. This may imply that downstream regulation of other structures of the network can be improved by using a different location for the first electrode. If there are multiple locations for the first electrode that have met other implantation criteria, then the downstream modulation can be seen as an additional criteria for selecting the best location of the first electrode. When additional electrodes are used, this method can be extended to review the effect of stimulation of the first electrode across multiple indirectly stimulated sites which are sensed by other electrodes. When multiple sites are selected, for either the first or second electrode locations in the first and second brain regions, then these may remain implanted and in the post-surgical period these alternative sites may be utilized and evaluated. For example, if a particular location does not seem to provide benefit to a patient over time (long term benefit) then an alternative location may be selected, used for treatment, and evaluated over a time period of weeks or months.

With respect to modulation of brain networks 106, during the post-surgical treatment of the disorder, the BMS must be programmed and the effects of neurostimulation assessed. BMS neuromodulation treatment protocols can be adjusted by patients or doctors, using an external patient programmer, to modulate the brain network in order to achieve and optimize therapeutic efficacy. Treatment protocols can also be adjusted based upon data sensed by the implanted sensors, according to rules used by the BMS.

In one embodiment, neurostimulation parameters can be set by the medical personnel based upon the results of functional imaging. The neuromodulation parameters can be adjusted until the target regions are modulated in a desired manner. For example, activity in regions of the network is increased, decreased, or otherwise altered. The results of the functional imaging can be analyzed using path analysis or other analysis which provide a model of the neural network being modulated, and the neuromodulation protocol can be iteratively adjusted until, for example, the model indicates normalization, in other words, that a characteristic of the brain network more closely approximates that found in normal control subjects or is otherwise maintained within a specified range.

Neuromodulation treatment can occur continuously, periodically, in response to patient demand, or responsively due to evaluation of sensed data. Additionally, a first protocol can be used for continuous or periodic neuromodulation, while a second protocol which is used in response to patient demand, or in response to evaluation of sensed data, is interspersed with or is used in combination with the first protocol.

With respect to evaluating treatment of the brain networks 108, evaluation can occur by comparing sensed data to reference data, which can be normative data, with respect to treatment criteria. Treatment failure may occur when brain activity of certain regions in the patient's brain deviate from the normative goals embodied by the treatment criteria, and treatment success may be judged by the return of the deviant features to within the normative range. Such change can be quantified by representing the patient's brain state as a multivariate vector (Brain State Vector, or BSV), in a multi-dimensional signal space and using the length of the BSV to quantify the distance from the normative region centered around the origin of the signal space. The BSV can be a vector computed as the difference between normative vector and an abnormal vector, or alternatively the BSV can be computed from z-scores and thus can be both statistically-based and normalized. Effective treatments should shorten the BSV, incorrect treatment may lengthen the BSV, and "side effects" may cause a change or rotation in the direction of the BSV in the signal space. The BSV can be computed upon the components of network model (e.g. SEM) wherein selected components best reflect the state of the disorder being treated. In other words, abnormal activity of the network is normalized or changed to bring an undesirable characteristic of the network closer to a desired level.

In one embodiment, if the desired changes are not reflected in either the subjective experience of the patient, or the data sensed by the implanted sensors, then the neural target area can be changed or an additional neuromodulation target may be chosen. However, it should be noted that alterations of neural firing patterns and adjustments in neurotransmitter and receptor systems which may play important roles in the therapeutic effects of brain stimulation, may have slow time courses, evolving over days or weeks, and accordingly evaluation may not be possible during a single surgical session. In other words, stimulation may not immediately manifest therapeutic benefit. Further, initial parameters may have to be altered should adaptation occur as neurostimulation continues over time. At the end of the surgical procedure, or during a follow-up session which occurs at a later time, surgical closure occurs with the various components of the brain neuromodulation system being adjusted and secured within the patient, so that surgical recovery can be initiated.

Evaluation of sensed data may indicate that stimulation of two or more regions of a brain network does not meet a treatment criterion. A treatment criterion can be, for example, that some characteristic of neural activity (e.g., power in a certain frequency band, neurotransmitter levels) must remain above or below, a specified value. For example, evaluation of sensed data may indicate that stimulation of a neural target may not have reached treatment criteria for one or more regions of a brain network. One type of evaluation of sensed data which could cause a change an existing, and/or evoke an additional, neuromodulation protocol, is a "network event". An example of a network event is when two or more regions of a network fail a treatment criterion with respect to each other. For example, a treatment criterion may state that brain region 1 must demonstrate an average value of a characteristic which is X % above that of brain region 2 (e.g., Brodmann area 25 must have 15% lower activity levels than Brodmann area 10). Network events occur when sensed data indicates that the neuromodulation treatment has failed to produce the desired modulation in at least one characteristic (e.g., activity level, correlation,) between 2 areas of a brain network. Network events can be constrained by conditional rules which govern the evaluation of sensed data. For example, a conditional rule may state that a network event must occur for at least a specified duration before a criterion is considered to have been passed or not met. The treatment criteria used to evaluate sensed data with respect to network events can utilize simple thresholds, statistical criteria, population or self-norm data, and may rely upon the output of modeling algorithms which compare the results of modeling of current data to target values for the model, to see if the treatment criteria have been met. The detection of network events can occur due to the evaluation of sensed data using treatment criteria and can occur automatically in the processor of the control subsystem of the BND.

With respect to evaluation of treatment 108 of FIG. 2A, the evaluation can occur according to a treatment protocol, which may cause sensing to occur, for example, at certain times, at certain intervals, in response to a medical event, at times dictated by an equation, continuously, periodically, in response to patient demand, or in response to sensed data (i.e., in a closed-loop fashion). Evaluation of treatment can occur during neuromodulation using the methods just described for Step 106. Evaluation of treatment can also occur at regularly scheduled times, for example, at 2, 4, and 6 months and then longer periods thereafter if treatment is deemed to generally be effective. If neuromodulation immediately and lastingly produces the desired therapeutic benefit, then evaluation of treatment does not need to occur.

With respect to modification of stimulation parameters 110, as stated, the evaluation of treatment which may lead to modification can occur, for example, continuously, responsively, or, periodically, and modification will depend upon the results of this evaluation. Modification of neuromodulation treatment 110 can occur using the methods described for Step 106. Modification of stimulation parameters can also occur due to time of day, due complex regimens programmed by medical practitioners, and/or due to an evaluation session in which the medical practitioners decide that modification is warranted. Other methods for modifying neuromodulation protocols and parameters, to improve the modulation of brain networks underlying unwanted aspects of a brain disorder, are discussed in other areas of this application including the use of stimulation linking rules and also the use of strategies for decreasing adaptation effects, which discusses distributing the stimulation across the brain network.

Generally, the method of FIG. 2A solves a problem of prior art which teaches neuromodulation for treatment of various brain disorders as if these each are due to a single area of abnormal activity, which is not part of a network. The methods of FIGS. 2a-i are primarily designed with a consideration of the indirect the changes which connections between the nodes of the network produce due to stimulation of these nodes. The NBN methods of FIGS. 2a-i also address the fact that disorders are usually not constrained to a single unwanted characteristic. Multiple unwanted features often characterize a single brain disorder, sometimes simultaneously, but also not, and also to varying degrees. Accordingly, stimulation of a network should differentially treat characteristics of a disorder by specifically modulating areas of the brain that primarily different characteristic of a disorder. In the case of depression, the different characteristics may be sadness, hopelessness, anxiety, antipathy, frustration, indifference, helplessness, or lethargy. Although there is obviously not a one-to-one mapping of these features of the disorder with brain structures, the idea is that stimulation to treat one area should compensate for the effects of this modulation on other areas so that other features are not unintentionally augmented. Characteristics of other disorders for which treatment is sought may be, for example, obsession, compulsion, inattentiveness, hyperactivity, and memory deficits whether recent, short term or episodic. Generally, methods for treating patients with a brain disorder comprises neuromodulation of at least 2 regions of a brain network, one of which has been at least partially associated with an unwanted characteristic of a brain disorder. While a particular region is being stimulated, the other brain regions are modulated in relation to the stimulation of this region. In this way, the successful treatment of one characteristic of a disorder will not cause changes in a different characteristic, as a side effect of treatment.

Figure 2B:
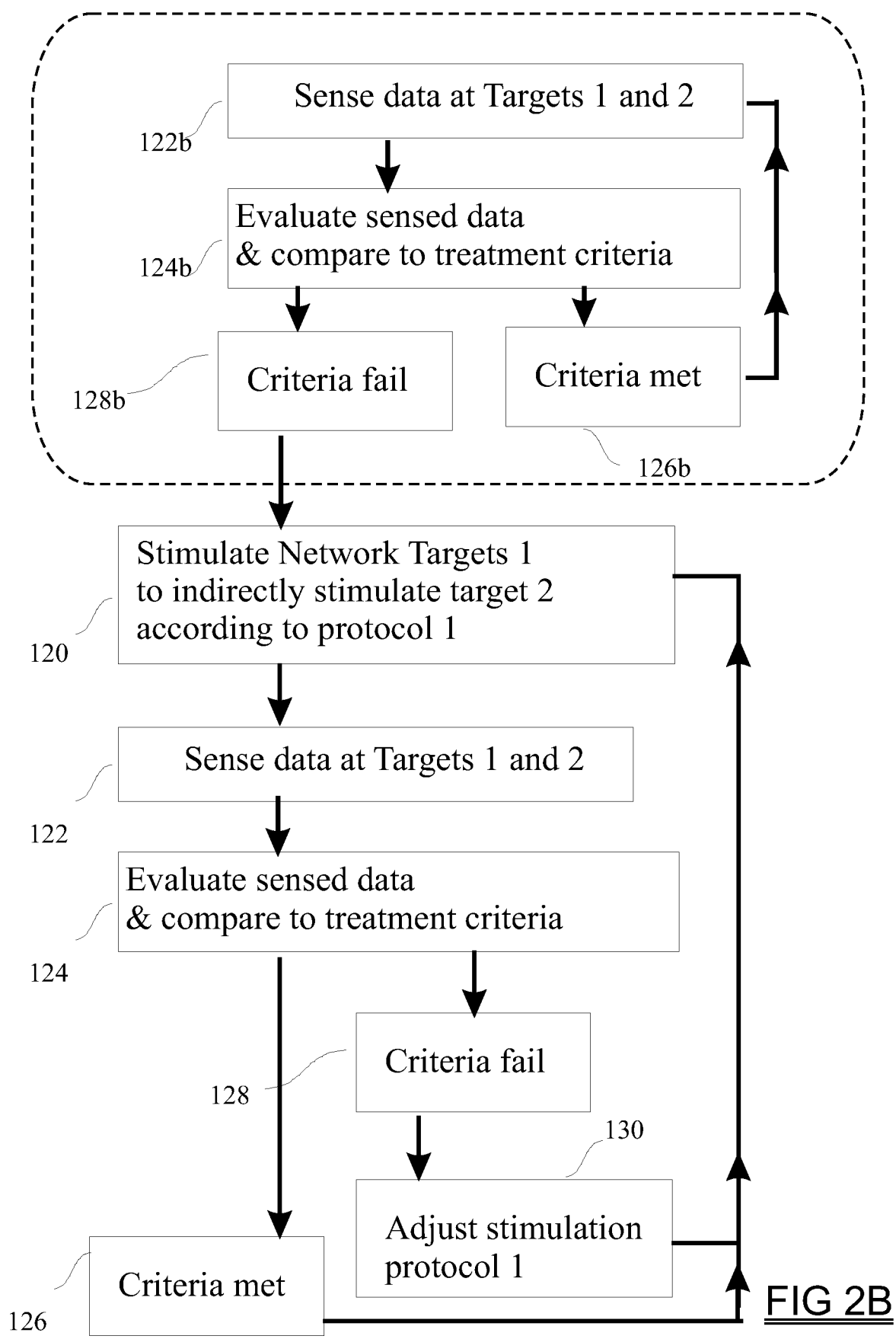
Figure 2C:
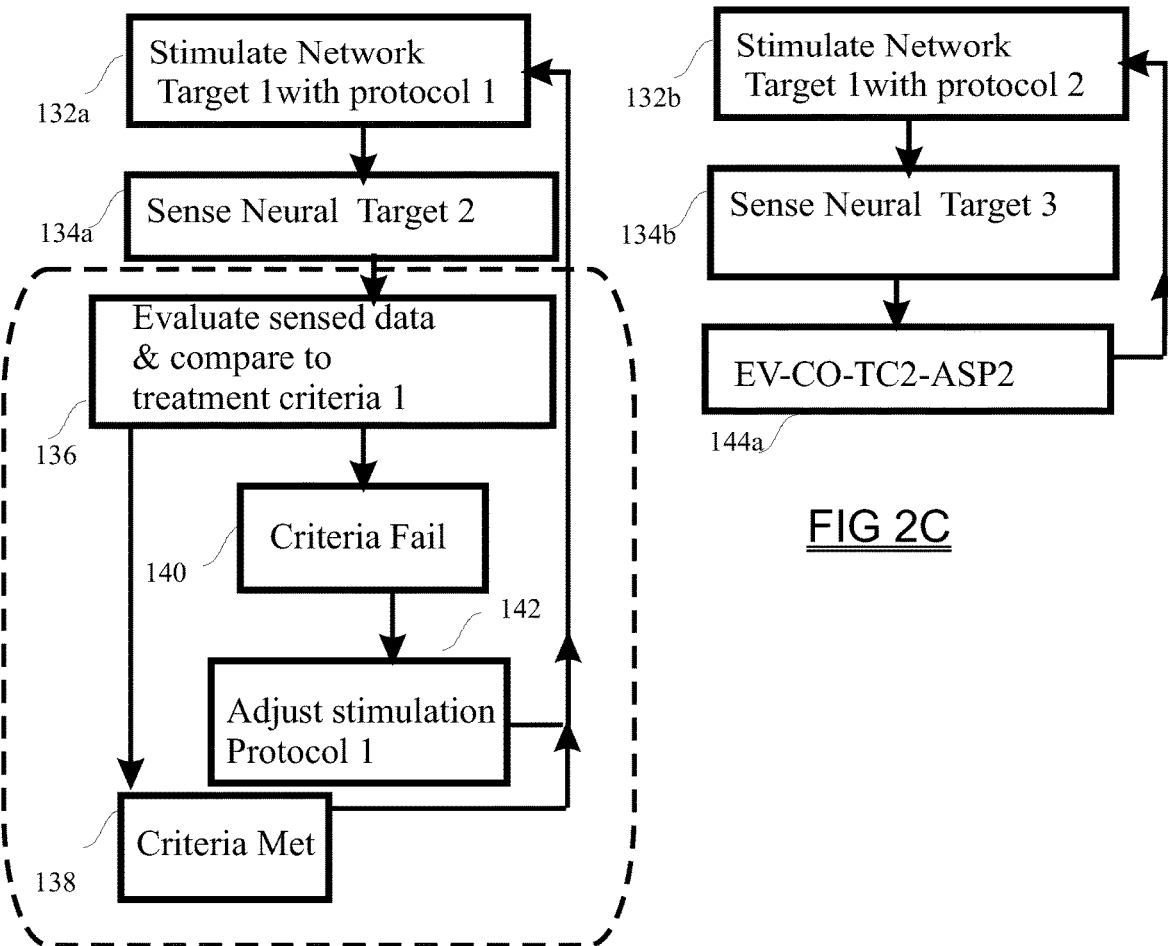
Figure 2D:
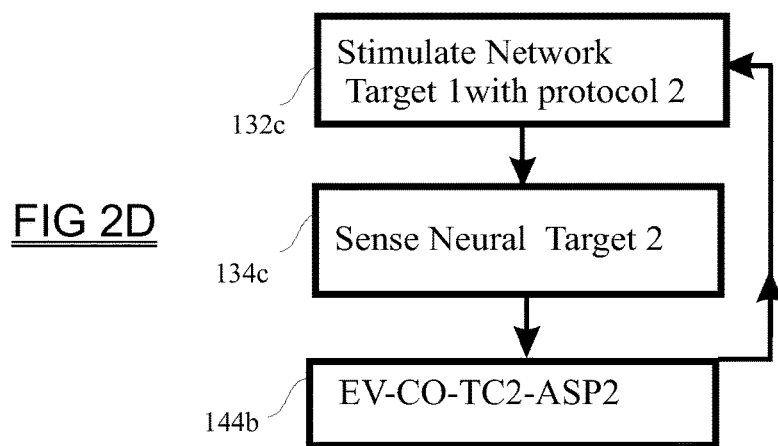

In another embodiment, a method of neuromodulation of a brain network for the treatment of a brain disorder includes providing stimulation to a target brain region of the brain network according to a stimulation protocol that produces neuromodulation of the target area as well as modulation of a second brain area of a network, the second area being sufficiently distal from said stimulation that it is not directly modulated by said stimulation 120, (of FIG. 2B). The method may only be step 120, or may also comprise sensing data and adjusting the neurostimulation protocol. These additional steps can include sensing data from at least regions 1 and 2 122, evaluating the sensed data using treatment criteria 124, adjusting said stimulation protocol if one or more of the treatment criteria fail to be met 130, such as the measure of activity in the first and second brain regions being within a specified range, and then repeating stimulation. The treatment in FIG. 2B lower, is for a continuous stimulation protocol. Of course, this protocol can be made responsive by including the subroutine within the dashed lines, which contains steps 122b-128b, wherein stimulation is not initiated until evaluation of sensed data indicates 124b this is necessary 128b. It is obvious that this routine, or a similar routine can be easily appended to the other methods described herein and shown in other figures. In another embodiment, illustrated in FIG. 2C a first stimulation protocol can be used for stimulating a target region of a brain network (e.g., C in FIG. 3G) 132a so that a desired change also occurs in a second region of the network (e.g., A in FIG. 3G). Step 132a can comprise the entire method, where the stimulation protocol is designed to stimulate not only the neural target, but also a secondary area of the brain network, in a desired manner. Additionally step 132a can be incorporated into a feedback method, where data is sensed 134a by a sensor in a second neural target in order to adjust the stimulation protocol according to steps 136-142. Further, a second stimulation protocol can be used to modulate the same target region 132b in order to provide a desired change a third region of the network (e.g., B in FIG. 3G), said change being sensed 134b, and the stimulation parameters being changed if dictated from evaluating the sensed data 144a. Step 144 includes the subroutine that is comprised of the steps located within the dashed area of the figure, the notation being evaluate the sensed data (EV) & compare (CO) to treatment critera2 (TC2) and adjust stimulation protocol #2 (ASP2) if needed. The portion of the stimulation protocol on the left side of FIG. 2C may be combined with the stimulation protocol illustrated in FIG. 2D, wherein a different change occurs in the second brain region of the network due to steps 132c, 134c, and 144b. The stimulation protocol used at one part of the network can be adjusted to differentially stimulate other parts of the network since different stimulation parameters will modulate different subgroups of neurons within the target area, which consequently provide differential modulation of other parts of the network. The adjustment of stimulation protocols in one region, based upon the effects of stimulation at a target area on other parts of the network is novel over prior art which has largely ignored secondary effects of stimulation (e.g., the fact that specific regions of a network can modulate activity in other regions). By stimulating at least one brain region of a network and sensing data from other parts of the network located relatively distal from the field of stimulation, the stimulation can be adjusted (e.g., through trial and error or based upon a network model) to produce the desired secondary effects (or additional stimulation can be provided to counter secondary modulation of these other areas).

In another embodiment, neurostimulation can occur in response to sensed medical events. A medical event can be detected, for example, using a template matching strategy or algorithm which can produce a probability score that an event has occurred, where when the probability score is above a specified threshold the event is considered to have occurred. Alternatively, the medical event algorithm can simply provide a true/false indicated that the event has occurred. The medical event can be, for example, a seizure, a network state, the approximately simultaneous drop in activity at a number of sensors which indicates a change in the network state. In this case, the absence of a medical event is evaluated as meeting a treatment criterion, and the detection of a medical event is evaluated as the failure to meet a treatment criterion. For example, if stimulation was occurring before the medical event occurred, detection of the medical event can lead to a change in the stimulation protocol, or the addition of a responsive stimulation protocol. Alternatively, if stimulation does not occur continuously (or at least periodically), then detection of a sensed medical event can cause stimulation to occur. When stimulation is initiated, this can occur at two or more areas of the brain network, and can be guided by linking rules.

Figure 2E:
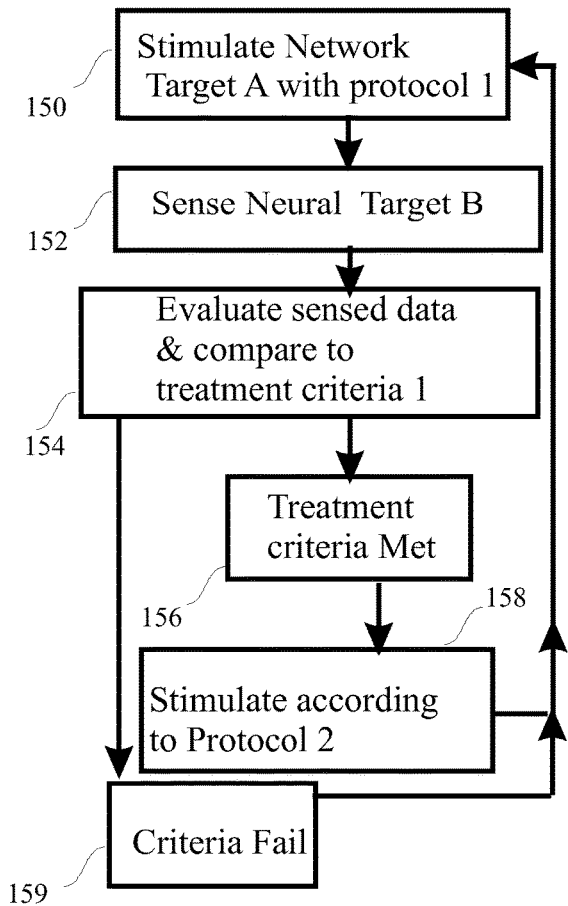
Figure 2F:
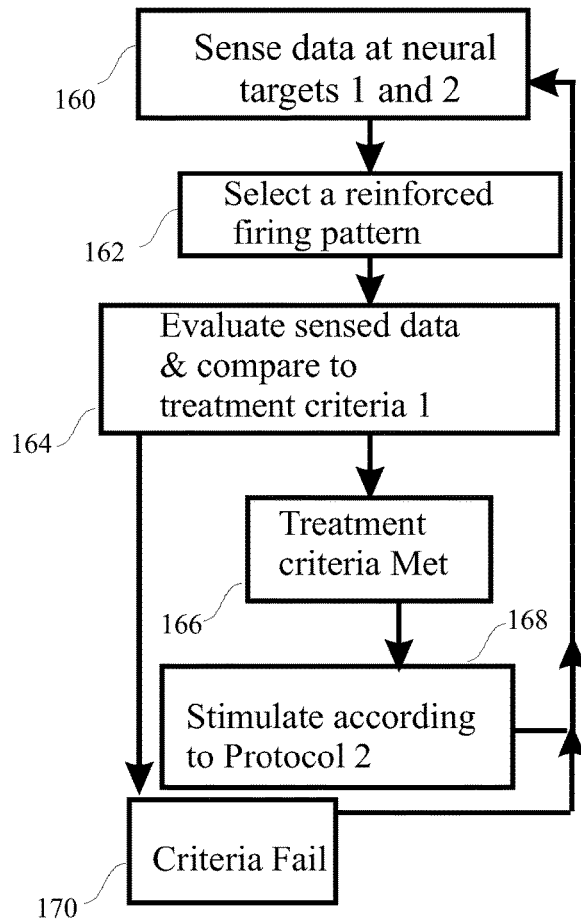

In another embodiment, an example of which is illustrated in FIG. 2E, neurostimulation of the network is provided in order to either increase or decrease the connectivity of the network by training using a Hebbian strategy. For example, stimulation can occur according to a protocol 1 at neural target A ("NtA") 150, while data is sensed at neural target B ("NtB") 152. When stimulation of NtA leads to increased activation of NtB (i.e. the activation occurs rapidly enough at NtB that it is likely due to activation of NtA) as defined by a criteria 156 then the neurostimulator stimulates according to stimulation protocol 2 158, which in this case is stimulating NtB in order to increase the synaptic connectivity. If the treatment criteria fails 159, then stimulation of brain region 1 150 again occurs, after adjustment if indicated. Further, stimulation of an area can be used to reinforce a particular type of firing pattern in the neurons of that area. In one method, an example of which is shown in FIG. 2F, a sensor is located in both NtA and NtB, and sensed data is obtained from both regions 160. Select a reinforced firing pattern 162, which can occur in several manners as is known to those skilled in the art. Various schedules of reinforcement can be implemented, including aperiodic, contingent, etc. In one method, a histogram can be generated wherein, for example, the counts for each of the different classes of neural firing patterns in NtA are added to the histogram whenever the firing pattern in NtA is followed by an increase in activation (or a desired firing pattern) in NtB. The class of neuronal firing in NtA which is most likely to provoke a change in firing in NtB will have a higher count in the histogram than other types of firing patterns which do not evoke changes in NtB, and this firing is the "reinforced firing pattern". Accordingly, treatment criteria 1, acts to reinforce the firing pattern when it occurs 166, by stimulating according to stimulation protocol 2 168 whenever the pattern to be reinforced occurs at NtA, where providing stimulation protocol 2 168 consists of stimulating area NtB to strengthen this association. Alternatively, stimulation protocol 2 168 can be stimulation of NtA which occurs to reward and reinforce the occurrence of this desired firing pattern. In this manner the strength of the connectivity of at least 2 regions of the network can be strengthened. This type of reinforcement is intended to 'retrain' a part of a brain network and can lead to a decreased need for subsequent stimulation therapy.

The reinforced firing pattern can either be intracellular, obtained from micro-tipped electrodes, or can be ensemble activity (spikes) as recorded in local field potentials (LFP), with the band width and gain of the sensing amplifiers set accordingly. When micro-electrodes are used, then the reinforced firing patterns can be based upon post-time histograms (PSHs) or identified patterns of spikes, where time zero for the PSH at NtB is determined by (time-locked to) stimulation at NtA. This level of firing pattern analysis within the—BMS is computationally high. A computationally less complex manner of examining the response of NtB to stimulation at NtA is to compute the time-locked narrow-band spectra of the activity recorded at NtA, where an increase in a certain firing pattern will result in an increased spectral power in respective bands, or will have a specific signature detected by time-frequency and/or wavelet analysis (wavelet packet or complex wavelet analysis).

Sensed data can relate, for example, to at least dopamine, serotonin, GABA or other neurotransmitter level, chemical or electrical activity of a neural population or group of cells, a neurotransmitter metabolite level, a medication or drug level, a hormone level, a blood-borne substance level. Sensed data can also relate to the relative levels of one or more measurements made, either within, across, or between brain regions, or can relate to a change in these levels over time.

Identification of Brain Networks and Adjusting Stimulation Parameters

The identification of numerous brain networks which putatively underlie (i.e., correlate with symptoms of) various brain disorders has come from many areas of neuroscience. Anatomical studies utilizing animal or post-mortem brains, or structural imaging, including computerized tomography (CT), magnetic resonance imaging (MRI), and its variants such as diffusion tensor imaging (DTI), have provided direct and indirect evidence of the role of brain networks, and the individual brain regions of these networks, in normal functioning as well as in various brain disorders. Functional imaging techniques which are accomplished with external sensor or techniques with use acutely or chronically implanted electrodes or neurochemical sensors, and pharmaceutical manipulations have all provided valuable data related to the metabolism, activity, connectivity, and neurochemistry of these brain networks. The targets of the network to be used for neuromodulation treatment can be identified from the results of these previous studies, functional neuroimaging of the patient's brain, or a combination of the two. Prior studies which can be used for identifying brain networks related to pathological affect, can include studies where healthy volunteers were asked to experience an emotion (e.g., sadness, anxiety).

There are many recent imaging studies which have identified brain networks underlying various disorders. In a series of studies, Northoff, and colleagues (2000, 2002, 2004) have used both fMRI and MEG to investigate brain networks for disorders such as Catatonia (a psychomotor syndrome characterized by concurrent emotional, behavioral, and motor abnormalities), and brain networks related with positive and negative emotions. With respect to Catatonia, pathophysiological mechanisms related to abnormal emotional-motor processing were examined in prefrontal cortical networks, while subject viewed pictures having positive or negative valence. Catatonic patients showed alterations in their orbitofrontal cortical activation pattern and also in functional connectivity to the premotor cortex in both negative and positive emotions, compared to psychiatric and healthy controls. Catatonic behavioral and affective symptoms correlated significantly with orbitofrontal activity, whereas catatonic motor symptoms were rather related to medial prefrontal activity. While imaging data may have shown abnormal activation in specific regions, there seemed to be two different networks that correlated with different aspects of the disorder. Thus, each characteristic of the disorder may be treated by primarily modulating the network correlated with the target symptom (and also by countering any unwanted modulation of one system by another which occurs in response to neuromodulation intended primarily for either system). In other words it is not enough to merely look for abnormal hyper-hypo activation, but rather treatment can target the regions of networks which are related to the symptoms for which treatment is sought. Further, not only activations, but also connectivity was found to be altered, suggesting that modulation of the interactions of neural areas engaged by the network may be just as important as normalization of activation, in the treatment of the disorder.

Lastly, the affective catatonic symptoms were closely related to dysfunction in the orbitofrontal cortex, while the alteration related to medial prefrontal cortical network was more associated with emotional processing. Again, the target regions of the brain network should be chosen, and neuromodulation provided, according to the treatment goals. Northoff (2002) has also implicated this prior brain network using Lorazepam, an antidepressant, which led to the reversal in orbito-frontal activation patterns. Further Northoff (2000) demonstrated negative emotional processing can be characterized by strong and early medial orbitofrontal cortical activation, whereas positive emotional processing showed rather later and weaker activation in lateral orbito-frontal/prefrontal cortex. This study is important because it argues for a functional dissociation between medial and lateral orbito-frontal/prefrontal cortex during negative and positive emotional processing, lending additional support to the assumption of a functional subdivision of two separate brain networks within the orbitofrontal cortex. Further it shows a temporal dynamic of a network, where the timing of the activations of different parts of the network and the modulation of temporal order of these processes, could be utilized in treatment.

In the case of schizophrenia, and other complex psychiatric disorders, across the population the disorder may engulf a cluster of heterogeneously distributed symptoms, traits, states, and symptoms. Further, within a single patient, several different networks may be primarily responsible for different characteristics of the disorder. For example, using fMRI studies have found that a brain circuit, involving the right amygdale and the MPFC had functional abnormalities during processing of emotion, suggesting a viable brain network for which treatment of dysfunctional emotional behavior in schizophrenia may be applied (Takahashi, 2004). Tackling a different aspect of this disorder, an fMRI study related to visually guided saccades and antisaccades, reported involvement by cortical and subcortical networks (Matsuda et al, 2004), supporting a model in which the fronto-parietal circuit is related to the planning of saccadic eye movements that involve attention and control, while the fronto-striato-thalamo-cortical circuits connect to cortical region as a feedback network. Accordingly, since abnormalities in spatial attention and eye movement control observed in schizophrenia may therefore stem from dysfunctions in the fronto-parietal and fronto-striato-thalamo-cortical circuits, these brain networks are appropriate targets for treating attentional pathology in this disorder. Looking into yet a further aspect of this disorder, Schlosser et al (2003a,b), provided evidence for altered connectivity of brain networks underlying memory disorders in schizophrenia, for both treated and drug free schizophrenics using SEM analysis of fMRI data. The studies suggest that enhanced thalamo-cortical and cortico-cortical intrahemispheric connectivity may be due to a compensatory increase of neuronal connection strength (consistent with a model of cortical inefficiency in schizophrenic patients), or a deficient thalamo-cortical filter which does not segregate/gate information normally. Further, lower interhemispheric connectivity of the frontal and parietal association cortex was found and was suggested as the functional correlate of reduced cognitive performance in schizophrenic patients. Therefore, the data from these studies provides two networks for which abnormal path coefficients indicated abnormal coupling between structures as reflected by covariance measures. These two networks could contain regions for the sensors/stimulators of a BND, and neuromodulation can be used to provide therapy which is geared towards deterring the network from producing this characteristic of the diseased state. Further, stimulation could occur outside of the structures just described, for example in the thalamus, but treatment efficacy can be measured by normalization of these networks, from sensors located within the brain networks. Further evidence of relevant networks come from Hoptman (2004) who used DTI and a voxelwise correlation analysis, and associated compromised white matter (measured by fractional anisotropy) with impulsivity in schizophrenia, in the left postcentral gyrus, right superior/middle temporal gyrus, and bilateral fusiform gyrus. These areas may therefore comprise a fronto-temporo-limbic circuit that modulates impulsivity, at least within this patient population. Clearly different brain networks underlie the complex characteristics of psychiatric disorders and therefore neuromodulation may attempt to differentially normalize, or otherwise modulate, each of these in order to treat a separate aspect of the disorder. Treatment should be guided not only by considering activation, but also relative activation, compensatory mechanisms, and the normal/abnormal connectivity and interactions within the brain networks that underlie various characteristics of these disorders.

Recently, new techniques have emerged and are being applied to ascertain brain networks which are responsible for a large array of characteristics in normal, aging, and abnormal brains (Thompson et al, 2004). For example, using modeling techniques, brain networks have also been identified which may be relevant for the treatment of some pain disorders (e.g, one network includes cingulo-frontal cortex and the midbrain, Valet 2004), treatment of multiple sclerosis (Au Duong, 2005), and other disorders. Additionally, the right subdivision of the anterior cingulate cortex (ACC) and the dorsolateral prefrontal cortex (DLPFC) have been shown to be components of a neural network which is abnormal in bipolar disorder, and which plays a critical role in the completion of tasks requiring self-monitoring and inhibition, functions often noted to be altered in bipolar patients (Staci et al, 2004). The identification of these brain networks 102 permits stimulation to be provided to, and sensed data to be obtained from, relevant brain regions during the treatment of various brain disorders. Further, by providing statistical summaries of the normal and abnormal values for different measures in regions of the network, to which the relevant measures of a patient's brain network can be compared (e.g., using a Z-transform), the success of a stimulation protocol can be assessed 108, and subsequently adjusted based upon this comparison. For example, the stimulation parameters can be changed 110 if various treatment criteria are not met.

Using data collected from the patient, information about the brain networks can be created using modeling methods (structural equation modeling or "SEM", dynamic causal models or "DCM", brain electrical source analysis "BESA"), and correlation techniques (e.g., partial least squares "PLS"), where, for example, a relevant brain network can be identified 102 as the regions (reflected as imaged voxels of a neural region) which show covariance with a characteristic of the disorder (i.e. seed PLS). Accordingly, a brain network may be identified as a circuit which is established by imaging methods as correlated with at least one characteristic of a mood, anxiety, or other psychiatric or neurological disorder. The imaging methods can detect this correlation using an analysis such as path analysis or other correlation-based technique. Brain networks can be identified as a set of putatively interacting structures which seem to underlie (e.g., be correlated with) a disease state or trait. Brain networks can also be identified while a patient is provided with one or more medications in the treatment of a disorder, and can be identified used neuroimaging data obtained before, during, and/or after exposure to medication, or across different doses of a medication. Networks can also be identified during performance of a task, during rest, or during exposure to emotional or neutral stimuli. In summary, neuroimaging data collected over a wide variety of tasks and conditions may be used to identify regions of the networks 102 which will be modulated during treatment, locate appropriate regions, for example, to guide surgical implantation of sensors and stimulators 104, to define treatment criteria, to evaluate neuromodulation during treatment 108, and to adjust the neurostimulation protocol 110 when the evaluation of neuromodulation treatment indicates a change is necessary, for example, in order to meet treatment criteria.

Alterations in brain networks are not present merely in brain disorders, but also occur as a part of normal aging process. Analysis of fMRI data, for example, by PLS/SEM (Grady et al, 2003a,b; Grady et al, 2005) has suggested that both normal elderly and Alzheimers patients establish different networks than normal young controls during memory tasks, implicating compensational brain networks which may assist the hippocampus to adaptively compensate for age related decrements in neural resources. Interestingly, the metabolism or "functional activation" was normal in the hippocampus of the elderly, and it was only by examining the functional connectivity of the brain networks within which this structure was activated, that compensatory activity was detected. This provides further support that the relative activation of a region should be understood in the neural context of the activated brain network and functional connectivity of the network, as may be reflected as path coefficients in some neural modeling. A network may contain all the structures implicated in a disorder, or may contain only a subsection of the network responsible for a particular characteristic.

Figure 2G:
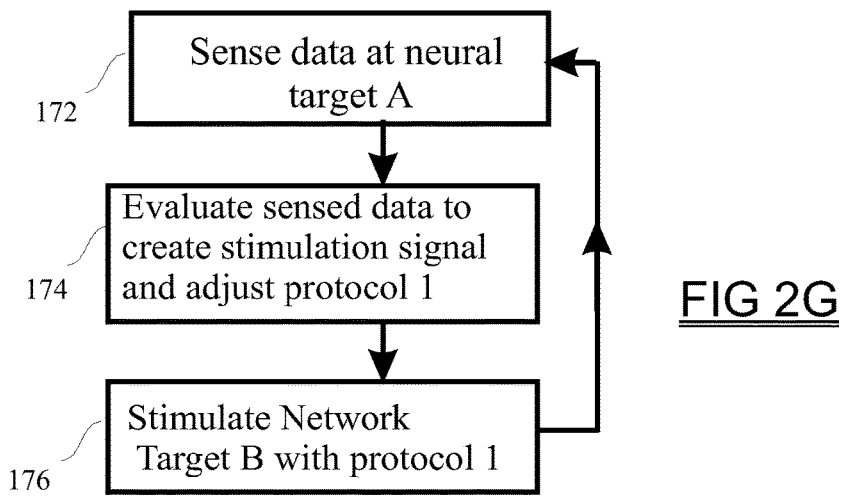

In one embodiment of a treatment protocol which addresses compensating for abnormal connectivity, the activity of one region of a network is used to guide the neurostimulation of at least a second region of the network. Rather than just increasing the activity of a second region of a network, the aim is to correlate the activation of this second region so that its activity is more (or less) correlated with activity in the first region, since neuroimaging data (such as network modeling, in normals, or population norms for imaging data e.g., QEEG normative profiles), indicates that the two regions are normally more coherent. For example, as illustrated in FIG. 2G a sensor can be placed in the first region of the network, and the sensed activity of this first region is obtained 172 and used to create the neurostimulation signal, or/and adjust the stimulation protocol 1 174, which is applied to the second region 176, thereby modulating the relationship between the two regions, for example, increasing their coherence. Adjusting the stimulation protocol 1 174, may include introducing a lag term into the stimulation protocol for the second brain region, so that it is stimulated with a lag. The lag may be based upon a self or population norm, and introduces a delay rather than having the intended activity occur in the two areas at substantially the same time. By changing the firing patterns, activation levels, or other characteristics of the second brain region of the network, that region can become more or less receptive to the input of the first region, and the stimulation will act to drive or entrain the activity of this second region so that afferent input from the first region is enhanced. Further, in some cases, if both the first and second regions of the network communicate with a third region, then by linking the stimulation of these two regions, their influence on a third region can be altered, e.g., become normalized. Accordingly, correlation analysis of data from brain networks can be used guide neurostimulation protocols, where the aim is not to increase or decrease the overall level of activity, but rather to alter the timing and correlation, of activity between the two regions of the brain network.

Pre-treatment imaging data may be used to determine sites of a network and stimulation parameters. The treatment may be one or more of psychological therapy such as cognitive-behavioral therapy, an ingested drug, neuromodulation by an implanted device. Post-treatment imaging data may be used to determine stimulation parameters, where the stimulation occurs at all sites or a subset of sites, while a patient is medicated or non-medicated, where stimulation has been recently turned off, or has been off for an extended period of time to permit symptoms to return.

In a set of specific examples of this method, imaging data can be statistically compared to prior datasets related to different types of prior populations. John et al (1994) has shown that topographic QEEG maps can be used to subtype disorders such as schizophrenia, into profiles that share common features. These feature clusters can be used to select appropriate pharmacological therapies based upon the successful therapies of prior patients who demonstrated similar profiles. Accordingly, in one method, imaging data of the individual is compared, for example, statistically compared, to a database, containing imaging data of individuals with different disorders and who have responded to different neurostimulation treatments, in order to classify the subject and provide the appropriate therapy. In one embodiment the imaging data is analyzed by software that provides a model of brain networks. These brain networks of the individual can be compared to a database of brain networks, in order to classify the brain networks of the individual into an appropriate subtype. Both implantation and subsequent treatment protocols can be based upon the classification of the features of the individual's brain networks with respect to the subtypes of the database.

Lastly, it should be noted that commonly known psychiatric (and other brain) disorders are largely thought to be heterogeneous, with individuals classified as having a particular disorder often manifesting unique clusters of symptoms. Further, the neural basis underlying a particular symptom may be different in different individuals. Although there is some evidence for final common pathway, or in other words, a common neural pathology which is shared by patients who manifest similar symptoms, clearly heterogeneous response to pharmaceutical treatment reflects that the overlap across individuals is not complete. Accordingly, when designing a treatment protocol (i.e., the targets intended for neuromodulation, the modality of neuromodulation, the drugs to be used, and the neuromodulation parameters) which is to be implemented, relying upon information about the brain network, rather than, or in addition to the behavioral symptoms, may provide for more accurate treatment. By evaluating the brain network of the individual, a direct measure of the pathology can be used to create an appropriate treatment protocol. For example, in one method, measures from a brain network of an individual can be statistically compared to different clusters in a database, in order to classify the network of an individual into a particular subclass. One type of classification can be related to treatment successes, wherein different subclasses of networks which have been shown to normalize when stimulation follows a particular treatment protocol are created. Classification of the patient, guides the selection of the treatment protocol for that individual. Accordingly, evaluating neural network data can be used to select the number, location, and type of neuromodulation that may be successful in normalizing the network, and consequently increasing the chance for providing successful therapy for the behavioral and cognitive symptoms of a disorder. In one method the steps for treating a brain disorder comprise; sensing neuroimaging data, evaluating neuroimaging data to provide at least one measurement of a brain network, performing a comparison of this measurement of a brain network to a database of two or more classes of brain networks and, using the results of this comparison to assist in selecting a treatment protocol including an implantation protocol.

Neuromodulation of Brain Networks in Treatment

During the post-surgical treatment of a patient, the parameters of the neurostimulation protocol can be iteratively determined by performing an assessment process, which examines changes which occur in the brain networks associated with the disorder. During the assessment process the creation of the neurostimulation protocol can be made based upon sensed data obtained from implanted sensors that measure the network's activity with respect to various aspects of electrical activation, biochemical or drug levels, neuronal firing, metabolism, and other measures for which sensors have been implanted. Alternatively, this determination can be used based upon sensed data which is neuroimaging data obtained from external sensors. Activation of different regions of the network, as well as other characteristics of the network can be obtained by modeling the imaging data and can be used to guide the neuromodulation protocol. The neuroimaging data can be sensed data that is collected during neuromodulation using a treatment protocol which stimulates the target regions, or only a portion of the neural targets, within at least one network which putatively underlies a characteristic of the disorder. This data can be used to determine the effects which stimulating portions of the network have on other portions. The treatment protocol can incorporate information about the inter-region interactions, for example, in the form of linking rules which change stimulation of 1 target region based upon the stimulation at least one other target region. Alternatively, treatment may be halted several seconds, minutes, hours, or days prior to the assessment procedure. Alternatively, sensed data obtained during both a "stimulation-on", and "stimulation-off" assessment period may be combined in the assessment procedure.

In another embodiment, the sensed data can be used to modify stimulation protocols, whereby the sensed data is processed to provide result data, and result data can be evaluated to adjust the neuromodulation protocol. For example, electrophysiological data is sensed from electrodes located in or near a structure of brain network. The sensed data is processed, for example, amplified and filtered, and the power within a specified band is measured to yield result data. The result data is evaluated, for example, compared to a treatment criterion, which may be based upon reference data. The success or failure of the result data to meet the treatment criterion will determine if stimulation parameters are maintained or adjusted, respectively. In another example, the result data are processed by mathematical models which evaluate the brain network, such as path models. This modeling produces result data which can be compared to treatment criteria in order to determine if treatment should be initiated, or, if already occurring, determine if it should continue with or without adjustment. The result data can be stored in a database (where it can then serve as reference self-norm data) located either in the implanted BND of the BMS or can be transmitted to a database which resides in external computer equipment such as an external patient programmer. The modeling algorithms can use information about endogenous electrical or chemical activity, or both. For example, MRS allows quantification of neurotransmitter levels in different regions of the network. Models of brain networks can be based upon neurotransmitter levels in several regions of a network, and the relative levels of these regions. Concentrations of a substance relative to the same or different substance in other brain regions (e.g., 5HT levels in region 1 vs GABA levels in region 2) can be used to guide the electrical, chemical or other type of neuromodulation of a target brain region.

Treatment may consist of preventing, deterring, ameliorating, or compensating for abnormal brain activity of a brain network which is putatively related to one or more aspects of the condition for which treatment is sought. Treatment can be provided for one or more brain disorders, for one or more brain networks, and the symptomotology can be can be a mixture of one or more pathologies. For example, clinical depression is a syndrome composed of a cluster of symptoms which may include negative mood, anxiety and somatic symptoms, apathy, vegetative and hormonal changes, motor slowing, and cognitive impairment. Treatment can be directed towards improving any one or more of these symptoms. Further, across different disorders, the symptoms for which treatment is sought can be either behavioral, cognitive, abnormal neuroimaging results, or a combination of these. Additionally, treatment can be oriented towards modulating brain networks related to both traits and states associated with a disorder, or which have been related to treatment refractoriness in a disorder.

Various methods of treating a brain disorders may comprise additional embodiments. For example, sensed data obtained from a sensed neural area may be used to modulate at least two target neural areas of a relevant brain network thereby treating the brain disorder. Alternatively, a least two sensors placed in two sensed neural areas of a relevant brain network may be used to adjust modulation parameters for at least one target neural area of a relevant brain network thereby treating the brain disorder. Further, neuromodulation for treating a brain disorder may simply consist of modulating at least two target neural areas of a relevant brain network. In another embodiment, neuromodulation of one or more target areas, using two or more neurostimulation protocols, results in the differential modulation of neuronal activity in one or more other brain areas of the identified brain network (e.g., see FIG. 2C and FIG. 2D). The modulation of at least one target area of a network can provide treatment by causing an increase, decrease, normalization, or other type of modulation in at least two other brain areas of the identified brain network. A brain network can be two or more brain regions which communicate with each other, and modulating the activity in a first region alters, at least a portion of the electrical or chemical characteristics of the second region.

The brain disorder which is to be treated may be a mood and/or anxiety disorder and at least one brain region for sensing or stimulating is a brain area in a network which includes a subcallosal area. The mood disorder may be selected from, for example, the group consisting of major depressive disorder, bipolar disorder, dysthymic disorder, or an anxiety disorder such as a panic disorder, posttraumatic stress disorder, obsessive-compulsive disorder or phobic disorder. The "subcallosal area" generally includes medial gray and white matter under the corpus callosum, as well as white matter tracts that are associated with the subcallosal area, afferent and efferent projections from the subgenual cingulate area, subcallosal gyrus area, ventral/medial prefrontal cortex area, Brodmann areas 10, 24 and 25, and closely adjacent neural tissue that regulates or is regulated by these structures. Accordingly, treatment should result in the desired modulation of activity in at least one brain area of an identified network which includes the subcallosal area as one of its structures. In one embodiment, the brain disorder is a mood or anxiety disorder and at least one target neural area and/or sensed neural is/are chosen from at least Brodmann 25, Lateral prefrontal cortex (LatF9), anterior thalamus, anterior cingulate, subgenual cingulate, orbital frontal cortex, hippocampus, and medial frontal cortex. Further, in order to modulate the symptoms of depression and anxiety, which often coexist within the depressive disorder, cortico-limbic pathways can be modulated wherein modulation selectively modulates dorsal cortical activity to modulate sadness, and ventral cortical activity to modulate anxiety (Liotti & Tucker, 1995).

Figure 2H:
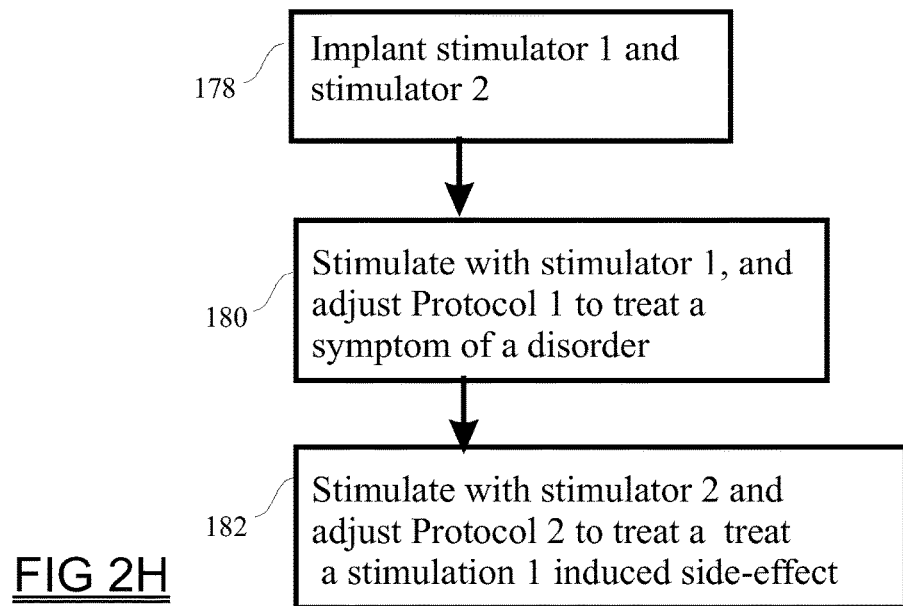

As mentioned earlier, a brain network can be comprised of several divisions (i.e., nuclei), within a particular brain structure. For instance, the cingulate generally acts as a relay nucleus which modulates activity between the cortex and limbic areas. Within the cingulate are many specialized subdivisions with unique properties and different roles, which are determined in part by the pathways which terminate within each area. For example, within the cingulate, Cg25 is a ventral division which is flanked by Cig24a-c as one moves away in an anterior-dorsal direction. Also, closely adjacent is the posterior cingulate (Cg30,Cg31). It is important to consider that divisions within a structure can modulate activity in other divisions of that structure, either directly, or via multi-synaptic pathways. The close proximity of different subdivisions within a structure increases the risk that the modulation (e.g., electrical field) of one structure can directly influence a different structure and result in unwanted side-effects. In other words modulation of one network can unintentionally cause the modulation of a different network since structure for the two networks reside in close physical proximity. One solution to this problem is a method of modulating a brain network, as illustrated in FIG. 2H which includes implanting at least a first stimulator and a second stimulator 178, adjusting a first modulation protocol and modulating a first brain area to relieve one or more symptoms of a brain disorder 180, and adjusting a second stimulation protocol and modulating a second brain area to relieve side effects produced by the modulation of a first brain area 182. In one example, the first stimulator, for simulating a first brain region is implanted in sufficiently close proximity to a second stimulator, which stimulates a second brain region, that the first stimulator directly modulates the brain area which is modulated by the second stimulator. The stimulation protocol of the second stimulator is adjusted to stimulate this second brain region so that this stimulation decreases unwanted side-effects produced by the neurostimulation provided by the first stimulator. The first and second stimulator can be two or more electrode contacts on a single electrical lead, each of which modulate the same brain network. Alternatively the method includes implanting two or more electrical contacts in adjacent brain regions, and providing a stimulation signal to the first contact to primarily modulate a first brain region in order to treat a symptom of the disorder, and providing a second stimulation signal to the second contact, to primarily modulate a second brain region, and adjusting the second stimulation signal to decrease the side-effects produced by the effects of the first stimulation signal Treatment of the network can be directed towards, and guided by, changes in the psychological or behavioral state of a subject, such as enhancing the subject's mood, or changes in the results of analysis of imaging data, including analysis of active regions, correlation analysis, partial-least squares analysis, and path analysis such as SEM. The analysis of a patient's brain activity can be used to guide at least one characteristic of treatment including the determination of at least one sensor location, target location, at least one characteristic of the stimulation protocol, at least one characteristic of the sensing protocol, and analysis protocol. The analysis protocol can utilize sensed data obtained from two or more regions of a network. During treatment, the sensed data from two or more regions of a network can be combined, compared, or otherwise incorporated into the analysis protocol, in order to determine if, for example, these regions are being relatively modulated in a desired manner or if adjustments need to be made to the stimulation protocol.

In addition to electrical stimulation, the BMS can utilize an infusion system configured to dispense one or more drugs in order to provide therapy to an abnormal brain network. The drug can be, for example, one or more of the following: a neurotransmitter agonist, a neurotransmitter antagonist, an inhibitory neurotransmitter upregulation agent. Pharmacological neuromodulation of two or more areas can be guided by linked rules in order to cause the relative activity to reach desired levels in these areas. Obviously, the BMS can be configured to dispense a drug to one target of a network and also to electrically stimulate a second target of the network.

In another embodiment, the system for stimulation of a network comprises at least one device having at least one sensor and at least one stimulator which can sense/stimulate at least one brain area of a pathological network. As shown in FIG. 4, the sensor can be part of a sensing subsystem 32 and the stimulator can be part of a stimulator subsystem 30, both of which may be coupled to a controller subsystem 34 in order to link the stimulating to sensing, and thereby provide responsive neuromodulation of a network to treat a characteristic of a brain disorder. The sensors and stimulators can be either functionally coupled to a BMS, or incorporated within it. If the neuromodulation is electrical the stimulator should include at least one electrical contact, and if chemical, then it should comprise at least one catheter. The stimulator can also contain a sensor for sensing data from one or more brain regions. The processor in the control subsystem may evaluate the sensed data and deliver neuromodulation according to a treatment protocol. If the brain disorder is a mood and/or anxiety disorder then at least one sensor and/or stimulator is located to permit stimulation or sensing of a brain region of the network, which includes a subcallosal area.

A "normal network state", occurs when the characteristics of a brain network, comprised of at least two brain regions, associated with an unwanted characteristic of a brain disorder, pass the one or more treatment criteria set for the network. An "abnormal network state" occurs when the characteristics of a brain network, of at least two brain regions, which are associated with an unwanted characteristic of a brain disorder, fail one or more treatment criteria set for the network. Neuromodulation treatment is designed to convert an abnormal network state into a normal network state, or to prevent, deter, or decrease the probability, frequency of occurrence, and severity of at least one abnormal network state. An individual may express a number of different types of normal and abnormal network states, due in part, to the existence of different endogenous states, for example, while awake and asleep (while the network may be vastly different between both these states, these may both be normal). The evaluation of sensed data can be used to determine when the network enters into a different state, for example, discriminant analysis can be used to classify the current state into one of several predefined states as defined, for example, by the medical personnel or normative data. "Discriminant analysis" per se, does not have to be the full analysis, but rather only the generation of a score used to classify the current state. Alternatively, a simple multivariate equation, template matching algorithm, patient input obtained from the external patient programmer, or other means can be used to quickly and accurately classify the state of the network without requiring the same amount of computational resources. Accordingly, different neuromodulation protocols and treatment criteria may be invoked during a number of different normal and abnormal states. This strategy is promoted by the evidence that neural activity of a region must be understood in the larger neural context of the network(s) of which it is a part, in other words the stimulation protocol and treatment criteria should be adjusted based upon activity across the network. In one embodiment of treating a brain network using neuromodulation, the steps for making the adjustment to the treatment protocol can comprise: sensing sensed data, processing sensed data to obtain result data, evaluating the result data to define a current network state; selecting treatment criteria associated with the current network state; evaluating treatment by comparing sensed data to treatment criteria and taking some action such as stimulating, or modifying the neurostimulation protocol if the treatment criteria fail to be met.

Neuromodulation treatment is not limited to increasing or decreasing activity of a region, but can also simply alter firing patterns of the region, for example, so that neurons increasingly fire in a burst or non burst mode, fire at a particular frequency, or fire only in response to activity at other areas of the brain network Treatment stimulation can aim to normalize an established brain network by sensing at least a first brain region and a second brain region, and stimulating at least a first brain region, according to data sensed in both of these areas, wherein said first brain region and second brain region have been shown to be part of a brain network underlying the a disorder for which neurostimulation is intended to serve as treatment. Treatment can also attempt to normalize a brain network associated with a brain disorder by sensing at least a first brain region and a second brain region, and stimulating in at least a first brain region, wherein stimulation of said first brain region is designed to a change in the activity of said second brain region. The change is a modification at least one characteristic of said neural activity, for example, a change in the dominant frequency, amplitude, or other change in the brain activity, or neurotransmitter level, of said second brain region. The modulation can use the data sensed in the first brain region to stimulate a second brain region, for example, in order to increase the coherence of the two regions. Neuromodulation can occur both chronically and/or responsively, in relation to changes in the network, or can occur according to patient request.

An alternative method of treatment which can include uniquely treating at least two symptoms of a patient with a psychiatric/mood disorder, and can comprise: implanting a control subsystem in the patient which control a stimulation subsystem which provides the delivery of at least two digital stimuli which are converted into stimulation signals to modulate at least two areas of the brain which primarily affect different symptoms of a disorder; and applying the at least two stimulation signals to at least two areas of the brain in order to alleviate, at least in-part, two or more symptoms of the disorder of the patient being treated. These brain areas can be part of a brain network, underlying two or more characteristics of the disorder, or can be part of different networks which do not interact. Further in this method, the stimulation of target structures which, for example, normally exhibit decreased activity which correlates with characteristics of the disorder, which is a depressive disorder, may be excitatory. Further in this method, the stimulation of target structures which, for example, normally exhibit increased activity which correlates with characteristics of the disorder, which is a depressive disorder, may be inhibitory. Additionally, in some embodiments, the at least two stimulation signals are applied to two or more targets of a network including the hippocampus, insula, right middle temporal gyrus, occipital cortex, temporal cortex, hypothalamus, anterior pituitary, posterior pituitary, right posterior temporal lobe, anterior thalamus, motor cortex, and premotor cortex.

In an alternative method, treatment includes inhibitory neuromodulation of at least two areas of a brain network correlated with symptoms of elevated mood and/or anxiety. Neuromodulation includes at least one stimulation signal which is transduced to provide stimulation to decrease excitement of the at least one area of this network which normally exhibits increased activity. In an alternative method, treatment includes excitatory neuromodulation of at least two areas of a brain network correlated with symptoms of elevated mood and/or anxiety. Neuromodulation includes providing at least one stimulation signal to provide stimulation to increase excitement of the at least one area of this network which normally exhibits decreased activity. In an alternative embodiment, stimulation to one region is excitatory, while stimulation to a second region is inhibitory. The stimulation can be applied, for example, to a network including one or more of the hippocampus, insula, right middle temporal gyrus, occipital cortex, temporal cortex, hypothalamus, anterior pituitary, posterior pituitary, and right posterior temporal lobe.

Neuromodulation of Brain Networks: Stimulation Linking Rules.

FIG. 3A shows a diagrammatic example of two brain regions A and B which represent target areas which are stimulated to treat a brain disorder. In this hypothetical example, stimulation treatment may occur at either brain region, and the stimulation protocol does not compensate or adjust for any interactions or connections between the regions, the assumption being that these are not relevant. This model reflects assumptions of the strategies used in the prior art, where neurostimulation of one region, for example A, is carried out without consideration of the effects of this stimulation upon other areas of a brain network, for example B. FIGS. 3B to 3G show alternative diagrammatic examples in which two or more brain structures are involved in simple brain networks. The solid lines represent positive correlations, where excitatory stimulation in one brain structure increases activity at another structure. The thickness of the line indicates the strength of the relationship. Dashed lines represent negative correlations, where excitatory stimulation in one brain structure decreases activity at another structure. Actual brain networks can consist of many more brain areas, and significantly more interactions, including reciprocal interactions, between these structures When stimulating brain networks the stimulation protocols of current invention can incorporate these interactions in order to more accurately and efficiently provide treatment, by differentially modulating different brain regions in an intended fashion. For example, linking rules can be used during neurostimulation treatment to adjust for one or more interactions between brain structures. Linking rules can also enable stimulation of the network to reinforce relative activity levels between different brain regions, by changing stimulation in one area as a function of stimulation provided, or data sensed, in another area. In some embodiments, linking rules may be adjusted over the course of treatment, as the interactions between structures change due to compensatory or other alterations in regions of the network. These adjustments can occur based upon sensed data which is evaluated in order to quantify the effects which stimulating one area has on other areas, and if these have changed, the linking rules are modified accordingly. Linking rules can therefore be used to address the effects of indirect or secondary stimulation. "Indirect stimulation" effects can occur at locations which are sufficiently distal from the site of stimulation that these areas are not directly stimulated by, for example, the electrical field of a stimulator. Instead, indirect stimulation can be mediated by stimulation of a first region which sends efferents to a secondary region, where the secondary region is part of a brain network of which the stimulated region is a part. Indirect stimulation relies upon, and adjusts for, connectivity between brain structures of a network.

It should be noted that the use of linking rules does not necessitate direct connectivity between the regions which are being stimulated. For example, in FIGS. 3C-3E a linking rule may modulate the stimulation of target A in accordance with stimulation of neural target B, in order to control the modulation of area C. Even though stimulation targets A and B are not directly connected, or do not directly influence each other, they both contributed to the excitation of area C, and so stimulation of each area should take into account simultaneous stimulation in the other area. Linking rules can become critical even when brain stimulation is applied to relatively separate regions in the brain. For example, linking rules can be applied in treatment which includes bilateral stimulation of contra-lateral structures, and may be used, for example, to synchronize or desynchronize two or more regions of the brain which reside in separate hemispheres.

It should also be noted that regardless of the strategy guiding the creation of the stimulation protocol, including the creation of stimulation signal itself (e.g., if its characteristics are generated in response to sensed data), which is to be used to modulate two or more regions of a network, this strategy can be altered according to linking rules. When control laws are used to govern the stimulation of different areas of a brain network, the selection and adjustment of these laws can be restricted by linking rules. Further, regardless of the methods used to process the sensed data and/or provide stimulation (e.g., use of neural network analysis, genetic algorithms, bayesian networks, decision trees, calculation of a measure of chaos, calculation of entropy, calculation of a maximal state control, calculation of seizure prediction, calculation of tremor size, calculation of relative activation levels in different parts of the brain) the use of linked rules can be incorporated. Linking rules can be used for both generating the stimulation signal and also for adjusting the neurostimulation treatment. Linking rules can also be relied upon for the stimulation of a single target area, if it is the case they these are used to adjust different protocols that are designed to indirectly modulate two areas of a network. For example, linking rules can guide the stimulating one target region using more than one protocol in order to obtain differential modulations of secondary regions where the time spent stimulating with each protocol is dictated by a linking rule.

Generally, linking rules which are to be used during the neuromodulation may be implemented based upon: data collected during assessment procedures; based upon normative data; or based upon the experience of the patient. In one embodiment, neuromodulation of a network occurs by modulating at least a first neural target region (i.e., NT1) and a second neural target region (NT2), which are part of a network underlying, or significantly correlated with, at least one characteristic of a disorder for which treatment is being sought. One example, of "linked stimulation" is that when at least one stimulation parameter for stimulating NT1, for example, voltage level, is increased by 1 volt then simultaneously the neuromodulation of NT2 is increased by 0.5 volts. Whenever NT1 is additionally increased by 1 volt, then NT2 is increased by 0.5 volts. The "linking rule" is that Vnt2=Vnt1*0.5, where Vnt1 is equal to the voltage used at target NT1, and Vnt2 is equal to the voltage used at target NT2. This rule could be used in the hypothetical system shown in FIG. 3E, where target A is stimulated with Vnt2, while target B is stimulated with Vnt1. In this case simultaneous stimulation of A and B results in no change in region C of the network. If A and C are both related to one the pathological characteristic related to the disorder, and A fails to meet a treatment criterion indicating that it is hypoactive, while C is almost hyperactive, then by normalizing A, without also stimulating B, C would become hyperactive. If area A is related to depression, while C is related to anxiety, then making C hyperactive could hypothetically cause the treatment of a symptom of depression to result in the emergence of, or an increase in, anxiety or mania. It is also possible that linked rules could have been used to directly stimulate region C with inhibitory stimulation, but stimulating B could be better in some instances. For example, if B is related to a different aspect of the disorder which could be treated, then providing stimulation at C would not enable modulation of B. In another example, an increase of voltage by 1 volt at NT1 leads to a decrease at NT2 of 0.5 volts. The "linking rule", in this case, is Vnt2=Vnt1*0.5*−1.

Multiple linking rules may be combined. For instance, these may be combined across stimulation of multiple neural targets of a network/: the voltage at NT2 can be determined by two other neural targets. A combined linking rule could be defined where an increase of 1 volt at NT1 leads to a decrease at NT2 of 0.5 volts, and an increase of 1 volt at NT3 leads to an increase in voltage at NT2 of 0.5 volts. In this case, the "linking rule" is Vnt2=(Vnt1*0.5*−1)+(Vnt3*0.5*), where if Vnt1=Vnt3, then no stimulation takes place at Vnt2 (or at least no adjustment in stimulation takes place at Vnt2 due to stimulation at these other 2 area). In another example, multiple linked rules may be relied upon simultaneously, where (Vnt2*0.5)*I=Vnt3 and (Vnt1*0.5)*E=Vnt3, may be used when NT2 is an area that is abnormally hyperactive, and which is upregulated by activity at NT3 (and inhibitory stimulation of NT2 compensates for secondary stimulation which is a side-effect of direct excitatory stimulation of NT3), and NT1 is an area that is hypoactive, and which is downregulated by excitatory stimulation at NT3, and NT3 is occasionally hypoactive and must be stimulated with excitatory neuromodulation. The designation "*I" and "*E" provide neurostimulation patterns that inhibit (suppress) or excite (increase) neural activity in the target region. Accordingly, without the linked stimulation rules, stimulation of NT3 in attempt to normalize the activity of that region, would cause the activity in NT1 and NT2 to become more abnormal, although other areas (e.g., NT4), may arbitrarily be correctly modulated by such treatment stimulation.

Linking rules are important because changes within the network, that occur as side-effects in other regions due to stimulation of a target structure, may aid, hinder, be irrelevant to, or may compensate for neuromodulation treatment in the target region. It various cases, these secondary changes may or may not be beneficial and may even act to modulate different symptoms of the disorder from the one that is intended for treatment. For example, Bench, Friston, Brown, Frackowiak, and Dolan (1993) used factor analysis on depressed patients' symptom ratings and identified three factors: anxiety, which correlated positively with rCBF in posterior cingulate and bilateral inferior parietal lobules; negative mood and psychomotor retardation, which correlated negatively with rCBF in the left dorsolateral prefrontal cortex and left angular gyrus; and cognitive performance, which correlated positively with rCBF in the left medial prefrontal cortex. Accordingly, if neuromodulation decreased anxiety by inhibiting activity in the posterior cingulate, and this led to changes in the left angular gyrus, then negative mood might be simultaneously increased as a side-effect. By also stimulating the left angular gyrus, both symptoms can be successfully treated in a selective manner. In another example, down-regulation of dopamine-based neural regions in the treatment of psychiatric disorders may co-occur with symptoms of movement disorders, since both A9 (extrapyramidal motor/nigrostriatal system) and A10 (ventral tegmental area VTA) are regulated by dopamine, although only the latter region is relevant to the positive symptoms of the disorder. If stimulation of a neural target, or treatment with an antipsychotic drug, caused decreased activation in both of these structures (e.g., see FIG. 3G, where downregulation of C decreases activation of both A and B), then this change would not be desirable in A9, since it merely leads to movement related abnormalities. Accordingly, inhibitory stimulation should occur in A10 while excitatory stimulation occurs in A9, to counter the downregulating effects caused by electrical or chemical modulation elsewhere in the network which affects both these structures. Similarly, in another embodiment, the fibers from the VTA which extend to the mesocortical system and the mesolymbic system can be differentially modulated, since these have been correlated with different symptoms of the disorder (i.e. positive and negative symptoms, respectively).

Using linked rules in the stimulation protocol to provide compensatory neurostimulation along the relevant fiber tracts, or within the different nodes that receive input from the VTA efferent fiber network, can compensate for stimulation of the VTA to increasingly restrict the resulting changes to the intended structures, while changes in other structures are inhibited or dampened. Alternatively, using two different stimulation protocols which selectively modulate different efferent fiber tracts of the network, which emanate from the same structure, is a method which could address this issue. Further, the time allocated for stimulating with one strategy could be determined by the time used for stimulating with the other strategy. Additionally, restricting the time allocated for different stimulation protocols can be provided by incorporating linked rules into the stimulation protocol where the linked stimulation characteristic is the amount of time for which the different protocols are used to stimulate a single region, rather than relating to protocols used in two separate regions In another example, the linking rule is again temporal, where for a given duration of stimulation in NT1, an associated duration of stimulation occurs for NT2. If stimulation at Nt2 occurs for a duration of the time that stimulation occurs at Nt1, the rule might be $Tnt2=Tnt1*0.5$, where the stimulation at NT2 lasts for 50% of the time that stimulation occurs at NT1. In another example, the linking rule is frequency related where the frequency of stimulation for NT1, determines the frequency of stimulation which occurs at NT2. If the frequency of stimulation at Nt2 occurs slightly lower than the frequency of stimulation at Nt1, the rule might be $Fnt2=Fnt1*0.95$, where the frequency of stimulation at NT2 is 5% slower than the frequency of stimulation which occurs at NT1. In another example, the linking rule is latency related where the start time of stimulation for NT1, determines the start time of stimulation which occurs at NT2. If the time of stimulation at Nt2 occurs slightly later than the time at which stimulation occurs at Nt1, then the rule might be $Lnt2=Lnt1*100$, where stimulation at NT2 begins 100 msec after stimulation begins NT1. It is obvious that the linked rules can be applied to any characteristic of the stimulation protocol, including pulse width, pulse frequency, pulse shape, stimulation time, frequency, voltage, current, and any other stimulation characteristic that determines the treatment stimulation. The linked rules can be determined, and adjusted, based upon the features of a model of the brain network which underlies the disorder, or the relationship between this model and a model of this same brain network in normal brains, where the intent is generally to cause a normalization of the impaired brain network of the patient (see John et al, 1994 Seminowicz, 2004; Mayberg 2005). In addition to abnormally low or high activity in a patient, relative to normal controls, in neural regions of the brain network, the interactions and relations between these regions can be used to guide the neuromodulation parameters. For example, linking neuromodulation in two areas can be used to attempt to increase the correlation (path coefficients), between two regions of a brain network, which is decreased (smaller path coefficient), reversed (path coefficient with an opposite sign), or missing (a path coefficient which is normally expected was not fit by the path model), in the impaired individual.

It should be understood that linked rules for stimulation can be used in combination with sensing. For instance, in one embodiment, neuromodulation of a network occurs by modulating at least a first neural target region (i.e., NT1) and a second neural target region (NT2), which are part of a network underlying, or significantly correlated with, at least one characteristic of a disorder for which treatment is being sought. Additionally, sensed data is obtained from a sensor which senses at least one neural sensed region (i.e., NS1), which may, or may not, be the same as one of the neural target (i.e., NT) regions. In this example, when the data sensed at NS1 indicates that the neuromodulation of the network is needed and at least one characteristic of the neuromodulation protocol of NT1, for example, voltage level, should be increased, then simultaneously the neuromodulation of NT2 is increased to 75% that of NT1 (since in this hypothetical example the linking rule was $Vnt2=0.75*Vnt1$).

Additionally, linked rules can be applied to sensed data of the brain network. For example, a first sensed neural region (i.e., SN1) and a second sensed neural region (SN2) may be used to determine the stimulation parameters of at least one target (NT1). If the characteristic sensed at NS1, affects the neural network three times more than a characteristic sensed at NS2, then the rule might be $Vnt2=k*(Vsn1*3+Vsn2*1)$, where stimulation at NT2 is determined as 3 times the voltage sensed at Vsn1 and 1 times the voltage sensed at Vsn2 times a constant which results in an output voltage that is related to the size of the sensed voltages and the characteristics of the measurement circuit. Accordingly, both stimulation and sensing linking rules can be based upon imaging data, sensed data, self-norms, and population norms, related to characteristics of the network to be treated. In this example, Vsn1 and Vsn2 could be the voltage in a particular frequency band, and Vnt2 can be an output voltage of an arbitrary stimulation signal that may not be related to the frequency band used to estimate Vsn1 and Vsn2. Alternatively, Vnt2 could be Fnt2, where it is the stimulation frequency rather than voltage that is adjusted based upon the linking rule. Vnt2 could also be a variable such as Bnt2, which is a measure of perfusion or blood-flow in that target area In other words, the linking rules can functionally relate different characteristics of the sensed and stimulation signals, and can be implemented cross-modally.

In one method, a model of the network is built by iteratively stimulating one or more areas of the network and measuring the effects on other areas of the network. For example, one step is to stimulate NT1 using 1 or more voltage levels or other characteristics of the stimulation signal and the next step is to examine changes which occur in the rest of the network. The next step is to adjust the neuromodulation protocols of other areas by incorporating linked-rules so that these other areas are stimulated using one set of protocols when NT1 is simultaneously stimulated (to counter the secondary effects), and another set of protocols when NT1 is not stimulated. By iteratively stimulating different areas of the network and recording the changes at other areas, a model, or a table of values, of the network and its response to different types of stimulation, can be created. This procedure can be done according to a protocol in the BMS, which may be operated in conjunction with instructions inputted by the patient using the external patient programmer and can occur in a primarily automatic and fixed manner, or can be adjusted, according to an algorithm or according to the decisions of a medical technician. The result comprise a set of transfer functions, which represent the effects/relationships between each pair of regions of the network, for the different types and levels of stimulation that exist in the stimulation protocol. These transfer functions can then be incorporated into a set of multivariate rules that guide neuromodulation of the network, as different brain areas are simultaneously stimulated. Using this method or other methods which may be more efficient, linking rules can be created and utilized by being incorporated into the neurostimulation methods and systems of the current invention.

It is obvious that linked rules for the evaluation of sensed data, as well as linked rules for the stimulation characteristics, can be combined to determine the resulting neuromodulation protocol characteristics. It should also be recognized that linked rules may be incorporated into algorithms, may be conditional, and can also be non-linear, and discontinuous, only being implemented across certain ranges. For example, a linked rule may be Vnt2=k*(Vsn1*3+Vsn2*1), while Vnt>2 volts and Vnt2=k*(Vsn1*5+Vsn2*1) while Vnt<2 volts. Linking rules can regulate using two different types of parameters. The voltage at NT1 can be determined by the voltage at NT2 and the frequency at NT2, for example, Vnt1=Vnt2 and if Fnt2>80 then Vnt1=Vnt2+((Fnt−80)*0.5), where the voltage at NT1 is equal to the sum of the voltage at NT2 and 0.5 volts for every additional 1 Hz, as the modulation frequency goes above 80 Hz. In another example, the frequency at NT1 can be set equal to the sum of a constant voltage and a term that varies as a function of the voltage at NT2. Linking rules can be used to set the initial stimulation parameters, and also relied upon during their adjustment during treatment, as may be required when evaluation of sensed data, or simply a treatment program defined in the stimulation protocol, indicates that such adjustment is needed. Accordingly, linking rules can be used during steps 106 and 110 of FIG. 2a.

Additionally, linked rules can be utilized by and incorporated into the external patient programmer. When using a patient programmer, and manually increasing the voltage in NT1, a linking rule can cause correct adjustments to occur in the stimulation parameters of other neural target regions. Further, in the same ways that current external programmers allow patients to adjust stimulation parameters, the linking rules can be adjusted by patients, within limits set by a physician.

Linking rules for sensing, evaluation of sensed data, and stimulation are important for accomplishing features of the invention. For example, these can be used to provide neuromodulation of one region of a brain network based upon the characteristics of another region of the brain network, or based upon the relative activity which is sensed across the two regions. Relative activity may be measured as the electrical energy across a certain frequency band, which is sensed in one brain region and assessed in relation to either electrical or chemical activity in at least one other brain region of the brain network. In other words, electrical energy in one brain region can be compared to chemical activity or chemical levels in another brain region. Further, neuromodulation of a first brain region can also depend upon combining sensed data from that brain region and at least one other brain region which has been shown to form a neural circuit. The linked rule can state that stimulation of area A must be increased until a measure that is sensed in area A is twice as large as the size of the measure sensed at area B, and can also state whether excitatory stimulation in area A must be increased, or stimulation in B must be decreased (or both must occur in proportion as specified in the linked rule), until this is true. In this case, the combined activity can be evaluated with respect to treatment criteria. Additionally, the use of linking rules and treatment criteria may be used in a number of manners to address, utilize, and compensate for interconnectivity of brain regions engaged by a brain network that is to be modulated in order to provide treatment.

Brain Network Strategies for Decreasing Adaptation Effects.

While there are known strategies for combating the emergence of adaptation to the neuromodulation, these usually employ methods that rely upon changing the neurostimulation signal over time within a specific region. Varying the stimulation signal aims to decrease the type of habituation that may occur using a chronic and non-varying signal. A unique solution to the problem of adaptation is to modulate areas of the network so that different parts of the network are stimulated at different times. Further, while certain areas are stimulated, a previously stimulated area may not be stimulated or may be stimulated at a decreased level. This strategy can utilize information about the connectivity and dynamics of a network in the creation of the alternative neuromodulation protocols. For example, if excitatory stimulation of a target region NT1 leads to increased activation at NT2 and decreased activation at NT3, and this differential modulation is desired, then it may be efficient and efficacious to simply stimulate NT1 and provide indirect modulation of these other structures (as well as being more efficient for a power supply). However, if the neural activity in NT1 demonstrates adaptation to the stimulation signal, as reflected by a decreased modulation of NT1, NT2 or NT3 over time (as can be reflected by sensed data values indicating that stimulation related effects, stored in the database memory 38, were drifting upward or downward over time), it may be beneficial to halt or attenuate stimulation at NT1 and initiate or increase stimulation directly at either NT2, or NT3, or both (or to provide indirect stimulation via a different structure which also modulates NT2 and NT3). Accordingly, either in response to sensed data which indicates adaptation has occurred, or simply according to a protocol which changes over time, stimulation can alternate the specific neural targets of the network which are stimulated, so that the overall desired neuromodulation of the network is approximately maintained. Using this type of dynamic and distributed strategy, for modulating regions of a brain network, offers advantages over, and can also be combined with, the know methods of treatment. In one embodiment, the neurostimulation protocol can serve to decrease the effects of adaptation by alternating stimulation according to evaluation of sensed data so that the linking rules for stimulation are maintained (e.g. adjust stimulation at two stimulators until sensed activity related to a relative measure is maintained within a desired range. The linked rules and the protocols can be contained within a database of the BND, and can be adjusted by the medical personnel or patient using the external patient programmer. Using information about the brain network can assist in circumventing adaptation effects by permitting stimulation of different regions to result in approximately similar types of modulation of the network. In the brain network represented by FIG. 3c, if sensed data indicates that modulation of neural target A begins to cause less of a change in C, then excitatory modulation of neural target B can be initiated, rather than increasing the amplitude of neurostimulation of neural target A. Further, in the brain network represented in FIG. 3e, if sensed data indicates that modulation of neural target A begins to cause less of a change in region C, then inhibitory modulation of neural target B can be initiated, rather than increasing the amplitude of excitatory neurostimulation of neural target A.

External Patient Programmer

The external patient programmer can enable the patient to communicate with the implanted neuromodulation device in manners which have been extensively described by known art. For example, the external patient programmer can allow patients to rate one or more symptoms or characteristics of their disorder, and also to modify neuromodulation parameters related to each aspect of the disorder. Unique from prior art however, are several features such as automatically adjusting stimulation to a second area if the stimulation in a first area is adjusted by the patient, as can be dictated by linking rules implemented by the device working jointly with the external programmer. This type of linked rule implementation may be invisible to the patient, for example, neuromodulation protocol related to the treatment of sadness may be best provided by adjustments for neurostimulation to areas NT1 and NT2, where if the patient chooses to increase modulation directed at these areas, this increase occurs proportionately for the two areas, as defined by the linking rule. Since it is a feature of the current invention to differentially modulate unique regions of the network, if modulation of a characteristic of the disorder relating to "indifference" may require modification of neuromodulation at NT3, NT2 and NT4. Accordingly, at least partially differential treatment of symptoms occurs by allowing patients to modify parameters primarily related to a particular symptom of their disorder. This may entail adjusting stimulation parameters only for a specific region of the network. For example, adjusting the treatment for "anxiety" may primarily cause modification of the protocol for neuromodulation of the posterior cingulate and bilateral inferior parietal lobules; adjusting the treatment of "negative mood" or "psychomotor retardation" would primarily cause modification of the protocol for the left dorsolateral prefrontal cortex and left angular gyrus, increasing the treatment of "cognitive performance" would primarily alter the protocol for stimulating the left medial prefrontal cortex. Furthermore, the patient programmer may allow patients to specifically modify the protocols related to hypothetical brain network 1, 2 or 3, each of which is primarily related to one or more aspects of their disorder. The patient programmer can also allow patients to modify linking rules, within tolerance levels which may be set by a physician.

TMS and Alternative Embodiments

It is well known that TMS (e.g., repetitive TMS or "rTMS") can be used to stimulate one or more brain regions, and therefore can be used to determine the utility of stimulating different networks in particular manners. This can be accomplished during an assessment procedure in order to evaluate different brain regions which may be candidates for implanted stimulators and sensors. Further, while the methods and system described herein have described using both implanted and external components, the invention can include TMS treatment for the neuromodulation of brain networks and can be completely external, although it may cooperate with implanted components. The methods described above are consistent with TMS treatment except that instead of implanting a device and providing an implanted stimulator which directly modulates neural tissue, the modulation is provided by the TMS equipment and protocol. In a general embodiment of the invention, TMS can used to modulate at least two neural targets which are part of a brain network, according to the methods described herein. In an alternative embodiment, TMS is used prior to implantation to test and detect regions and parameters which would the be provided by the implanted devices used during post-implantation treatment.

The BMS may be comprised of at least one device which is implanted in the subject's body. Alternatively, the BMS can rely upon one or more neurostimulators embodied within a single housing, or may be realized in a distributed design using spatially separate components which can be either implanted or external or a combination of these two. For example, two or more Bion™ stimulators, which may be controlled by a single computer system (or by a control subsystem of one of the Bion™ stimulators), can be implanted in the brain of a subject to stimulate at least two areas of the brain network.

SUMMARY

This specification has described a number of embodiments of methods and systems for modulating brain networks in the treatment of brain disorders. A central feature is that the methods of treating a characteristic of a brain disorder use a brain modulation system to modulate at least two regions of a brain network and the stimulation protocol for stimulating a first region is modified due to the stimulation protocol for stimulating at least a second region. Further, the stimulation protocol of a first region can be modified due to the sensed data of at least a second region. Both of these contingencies can occur using a stimulation protocol that is defined or adjusted based upon linking rules. When the BMS uses evaluation of sensed data to provide neurostimulation, the evaluation of sensed data can cause stimulation to occur responsively if sensed data indicates that a difference between sensed data and a target reference value, as can be reflected in a BSV, fails to meet a treatment criterion.

Further, the linking rules can incorporate values derived from a model of brain activity, an equation, an evaluation of sensed data, values obtained from a database. This feature therefore basically entails a method of implanting a brain modulation system and modulating at least a first region and a second region of a brain network, wherein the stimulation protocol of a first region is modified due to data sensed in, or stimulation that is provided at, at least a second region of the network. When the BMS contains a sensing subsystem, a stimulation subsystem, and a control subsystem, the control subsystem can contain the linking rules for guiding neuromodulation treatment in response to sensed data.

In another embodiment a method of treating at least one characteristic of a brain disorder comprises performing stimulation to increase the normalization of an established brain network. This can include the steps of sensing a first brain region and a second brain region, and stimulating at least the first brain region. The first brain region and second brain region comprise at least a portion of a brain network associated with a disorder for which neurostimulation is intended as treatment, and normalization is related to at least one of electrical and chemical activity.

In the methods described herein the brain disorder can be a mood and/or anxiety disorder and at least one sensed area is a brain area in a network which includes a subcallosal area. Alternatively at least one target area is a brain area in a network which includes a subcallosal area, but is not the subcallosal area itself. Further, the device provides at least electric, magnetic, chemical, optical or pharmaceutical treatment to achieve modulation of the brain activity. The mood disorder can be selected as a major depressive disorder, bipolar disorder, dysthymic disorder, or an anxiety disorder which is at least a panic disorder, posttraumatic stress disorder, obsessive-compulsive disorder or phobic disorder. Treatment also can be provided for a psychiatric disorder which is at least one of psychosis, schizophrenia, and obsessive compulsive disorder. The method of neuronal modulation of at least two target areas is intended to enhance the subject's mood.

The method of treating a brain dysfunction which is a mood and/or anxiety disorder, may treat disorders including panic disorder, posttraumatic stress disorder, obsessive-compulsive disorder and phobic disorder, and can include implanting at least one the two stimulators in a target area which is a subgenual cingulate area. Further, the target neural area and/or the sensed neural area can be chosen from at least one of: Brodmann 25, Lateral prefrontal cortex (LatF9), anterior thalamus, anterior cingulate, subgenual cingulate, orbital frontal cortex, hippocampus, and medial frontal cortex, and the brain disorder is a mood or anxiety disorder.

The described systems can be used for treating patients with obsessive-compulsive disorder and neuromodulation is of a brain network which includes the anterior limbs of the internal capsule. Neuromodulation can also occur for at least 2 regions, each of which has been at least partially associated with a characteristic of a brain disorder. Alternatively, neuromodulation treatment is of at least 2 regions, each of which has been primarily associated with a characteristic of a disorder. The characteristics of this disorder can be, for example, sadness, hopelessness, anxiety, antipathy, frustration, helplessness, lethargy.

Although the text of this specification often discusses treatment of at least one network, it should be understood that neuromodulation systems can be implanted bilaterally, and for a network in each hemisphere may be modulated based upon sensed data or other characteristics of the ipsilateral network. Alternatively, neuromodulation of a brain networks can be based upon sensed data, from the contralateral network, or may be based upon data sensed from structures in networks on both sides of the brain. Additionally, neuromodulation of a brain networks in one hemisphere can treat one characteristic of the disorder, while neuromodulation of brain networks in the other hemisphere can treat a different characteristic of the disorder.

All patents, provisional and pending applications, and publications cited herein, are incorporated by reference herein, as if included in their entirety. In the claims of this application, when methods have steps which have been assigned letters, the steps may occur sequentially in the order indicated by the letters, or certain steps may occur approximately simultaneously, or in an interleaved fashion, with other steps. The headers for various sections such as "Background" or "Treatment" are intended to be descriptive only, and do not limit the scope of the material which is provided in these sections.

REFERENCES

Abelson J L, Curtis G C, Sagher O, Albucher R C, Harrigan M, Taylor S F, Martis B, Giordani B. Deep brain stimulation for refractory obsessive-compulsive disorder. Biol Psychiatry. 2005; 57(5):510-6.

Au Duong M V, Boulanouar K, Audoin B, Treseras S, Ibarrola D, Malikova I, Confort-Gouny S, Celsis P, Pelletier J, Cozzone P J, Ranjeva J P. Modulation of effective connectivity inside the working memory network in patients at the earliest stage of multiple sclerosis. Neuroimage. 2005; 24(2):533-8.

Baker S C, Frith C D, Dolan R J. The interaction between mood and cognitive function studied with PET. Psychol Med. 1997; 27(3):565-78.

Bench, C. J., Friston, K. J., Brown, R. G., Frackowiak, R. S. & Dolan, R. J. (1993). Regional cerebral blood flow in depression measured by positron emission tomography: the relationship with clinical dimensions. Psychological Medicine 23, 579-590.

Cohen-Gadol A A, Britton J W, Wetjen N M, Marsh W R, Meyer F B, Raffel C. Neurostimulation therapy for epilepsy: current modalities and future directions. Mayo Clin Proc. 2003; 78(2):238-48. Review.

Cooper I S, Upton A R, Amin I. Chronic cerebellar stimulation (CCS) and deep brain stimulation (DBS) in involuntary movement disorders. Appl Neurophysiol. 1982; 45(3):209-17. [0178] Eytan D, Brenner N, Marom S. Selective adaptation in networks of cortical neurons. J. Neurosci. 2003; 15; 23(28):9349-56.

Fandel T, Tanagho E A. Neuromodulation in voiding dysfunction: a historical overview of neurostimulation and its application. Urol Clin North Am. 2005; 32(1):1-10.

Grady C L, Mcintosh A R, Craik F I. Age-related differences in the functional connectivity of the hippocampus during memory encoding. Hippocampus. 2003a; 13(5):572-86.

Grady C L, McIntosh A R, Beig S, Keightley M L, Burian H, Black S E. Evidence from functional neuroimaging of a compensatory prefrontal network in Alzheimer's disease. J Neurosci 2003b 1; 23(3):986-93.

Grady C L, Mcintosh A R, Craik F L. Task-related activity in prefrontal cortex and its relation to recognition memory performance in young and old adults. Neuropsychologia. 2005; 43(10):1466-81.

Gilliam F G, Santos J, Vahle V, Carter J, Brown K, Hecimovic Depression in epilepsy: ignoring clinical expression of neuronal network dysfunction? Epilepsia. 2004; 45 Suppl 2:28-33.

Hoptman M J, Ardekani B A, Butler P D, Nierenberg J, Javitt D C, Lim K O. DTI and impulsivity in schizophrenia: a first voxelwise correlational analysis. Neuroreport. 2004; 15(16):2467-70.

Imas O A, Ropella K M, Ward B D, Wood J D, Hudetz A G. Volatile anesthetics disrupt frontal-posterior recurrent information transfer at gamma frequencies in rat. Neurosci Lett. 2005 Oct. 28; 387(3):145-50. [0186] John E R. The neurophysics of consciousness. Brain Res Brain Res Rev. 2002 June; 39(1):1-28. Review.

John E R, Prichep L S. The anesthetic cascade: a theory of how anesthesia suppresses consciousness. Anesthesiology. 2005 February; 102(2):447-71. Review.

John E R, Prichep L S, Alper K R, Mas F G, Cancro R, Easton P, Sverdlov L. Quantitative electrophysiological characteristics and subtyping of schizophrenia. Biol Psychiatry. 1994; 36(12):801-26.

Kong J, Wang C, Kwong K, Vangel M, Chua E, Gollub R. The neural substrate of arithmetic operations and procedure complexity. Brain Res Cogn Brain Res. 2005; 22(3): 397-405.

Kossoff E H, Ritzl E K, Politsky J M, Murro A M, Smith J R, Duckrow R B, Spencer D D, Bergey G K. Effect of an external responsive neurostimulator on seizures and electrographic discharges during subdural electrode monitoring. Epilepsia. 2004 December; 45(12):1560-7.

Lefaucheur J P, Drouot X, Von Raison F, Menard-Lefaucheur I, Cesaro P, Nguyen J P. Improvement of motor performance and modulation of cortical excitability by repetitive transcranial magnetic stimulation of the motor cortex in Parkinson's disease. Clin Neurophysiol. 2004; 115(11):2530-41.

Liotti M, Tucker D M. Emotion in asymmetric corticolimbic networks. In: Davidson R J, Hugdahl K, editors. Hemmispheric Asymmetry, Cambridge: MITPress, 1995. pp. 389-423.

Maihofner C, Forster C, Birklein F, Neundorfer B, Handwerker H O. Brain processing during mechanical hyperalgesia in complex regional pain syndrome: a functional MRI study. Pain. 2005; 114(1-2):93-103.

Matsuda T, Matsuura M, Ohkubo T, Ohkubo H, Matsushima E, Inoue K, Taira M, Kojima T. Functional MRI mapping of brain activation during visually Guided saccades and antisaccades: cortical and subcortical networks. Psychiatry Res. 2004; 131(2):147-55.

Mayberg H S. Modulating dysfunctional limbic-cortical circuits in depression: towards development of brain-based algorithms for diagnosis and optimised treatment. Br Med Bull. 2003; 65:193-207. Review.

Mayberg H S, Lozano A M, Voon V, McNeely H E, Seminowicz D, Hamani C, Schwalb J M, Kennedy S H. Deep brain stimulation for treatment-resistant depression. Neuron. 2005; 45(5):651-60.

Mcintosh A R. Contexts and catalysts: a resolution of the localization and integration of function in the brain. Neuroinformatics. 2004; 2(2):175-82.

Mcintosh A R, Lobaugh N J. Partial least squares analysis of neuroimaging data: applications and advances. Neuroimage. 2004; 23 Suppl 1:S250-63.

McIntyre C C, Savasta M, Kerkerian-Le Goff L, Vitek J L. Uncovering the mechanism(s) of action of deep brain stimulation: activation, inhibition, or both. Clin Neurophysiol. 2004; 115(6):1239-48. Review.

Northoff G, Kotter R, Baumgart F, Danos P, Boeker H, Kaulisch T, Schiagenhauf F, Walter H, Heinzel A, Witzel T, Bogerts B. Orbitofrontal cortical dysfunction in akinetic catatonia: a functional magnetic resonance imaging study during negative emotional stimulation. Schizophr Bull. 2004; 30(2):405-27. Review.

Northoff G, Witzel T, Richter A, Gessner M, Schlagenhauf F, Fell J, Baumgart F, Kaulisch T, Tempelmann C, Heinzel A, Kotter R, Hagner T, Bargel B, Hinrichs H, Bogerts B, Scheich H, Heinze H J. GABA-ergic modulation of prefrontal spatio-temporal activation pattern during emotional processing: a combined fMRI/MEG study with placebo and lorazepam. J Cogn Neurosci. 2002; 14(3):348-70.

Northoff G, Richter A, Gessner M, Schlagenhauf F, Fell J, Baumgart F, Kaulisch T, Kotter R, Stephan K E, Leschinger A, Hagner T, Bargel B, Witzel T, Hinrichs H, Bogerts B, Scheich H, Heinze H J. Functional dissociation between medial and lateral prefrontal cortical spatiotemporal activation in negative and positive emotions: a combined fMRI/MEG study. Cereb Cortex. 2000; 10(1):93-107.

Peled A. From plasticity to complexity: a new diagnostic method for psychiatry. Med Hypotheses. 2004; 63(1):110-4.

Penny W D, Stephan K E, Mechelli A, Friston K J. Modelling functional integration: a comparison of structural equation and dynamic causal models. Neuroimage. 2004; 23 Suppl 1:5264-74. Review.

Prichep L S, Alper K R, Sverdlov L, Kowalik S C, John E R, Merkin H, Tom M L, Howard B, Rosenthal M S. Outcome related electrophysiological subtypes of cocaine dependence. Clin Electroencephalogr. 2002; 33(1):8-20.

Stefurak T, Mikulis D, Mayberg H, Lang A E, Hevenor S, Pahapill P, Saint-Cyr J, Lozano A. Deep brain stimulation for Parkinson's disease dissociates mood and motor circuits: a functional MRI case study. Mov Disord. 2003; 18(12):1508-16.

Stern Y, Habeck C, Moeller J, Scarmeas N, Anderson K E, Hilton H J, Flynn J, Sackeim H, van Heertum R. Brain networks associated with cognitive reserve in healthy young and old adults. Cereb Cortex. 2005; 15(4):394-402.

Schoenen J, Di Clemente L, Vandenheede M, Fumal A, De Pasqua V, Mouchamps M, Remade J M, de Noordhout A M. Hypothalamic stimulation in chronic cluster headache: a pilot study of efficacy and mode of action. Brain. 2005 February.

Schoenen J, Di Clemente L, Vandenheede M, Fumal A, De Pasqua V, Mouchamps M, Remade J M, de Noordhout A M. Hypothalamic stimulation in chronic cluster headache: a pilot study of efficacy and mode of action. Brain. 2005 Feb. 2;

Schlosser R, Gesierich T, Kaufmann B, Vucurevic G, Stoeter P. Altered effective connectivity in drug free schizophrenic patients. Neuroreport. 2003; 14(17):2233-7.

Schlosser R, Gesierich T, Kaufmann B, Vucurevic G, Hunsche S, Gawehn J, Stoeter P. Altered effective connectivity during working memory performance in schizophrenia: a study with fMRI and structural equation modeling. Neuroimage. 2003; 19(3):751-63

Takahashi H, Koeda M, Oda K, Matsuda T, Matsushima E, Matsuura M, Asai K, Okubo Y. An fMRI study of differential neural response to affective pictures in schizophrenia Neuroimage 2004; 22(3):1247-54.

Valet M, Sprenger T, Boecker H, Willoch F, Rummeny E, Conrad B, Erhard P, Tolle T R. Distraction modulates connectivity of the cingulo-frontal cortex and the midbrain during pain—an fMRI analysis. Pain 2004; 109(3): 399-408.

Vidailhet M, Vercueil L, Houeto J L, Krystkowiak P, Benabid A L, Cornu P, Lagrange C, Tezenas du Montcel S, Dormont D, Grand S, Blond S, Detante O, Pillon B, Ardouin C, Agid Y, Destee A, Pollak P; Bilateral deep-brain stimulation of the globus pallidus in primary generalized dystonia. French Stimulation du *Pallidum* Interne dans la Dystonie (SPIDY) Study Group. N Engl J. Med. 2005, 3; 352(5):459-67.

Walker-Batson D, Smith P, Curtis S, Unwin D H. Neuromodulation paired with learning dependent practice to enhance post stroke recovery? Restor Neurol Neurosci. 2004; 22(3-5):387-92.

Yianni J, Bradley K, Soper N, O'sullivan V, Nandi D, Gregory R, Stein J, Aziz T. Effect of GPi DBS on functional imaging of the brain in dystonia. J Clin Neurosci. 2005 February; 12(2):137-41.

Zhao X, Pasricha P J. Novel surgical approaches to fecal incontinence: neurostimulation and artificial anal sphincter. Curr Gastroenterol Rep. 2003; 5(5):419-24.

What is claimed is:

1. A method of guiding the provision of targeted magnetic neurostimulation of a patient suffering an unwanted symptom comprising:
   a. evaluating neuroimaging data that is magnetic resonance imaging data sensed from the brain of a patient;
   b. said evaluating neuroimaging data including operating a processor of a computer for calculating result data for at least one modeled functional connection measure value of a selected brain network model having a first brain region and at least a second brain region of said patient using said neuroimaging data;
   c. determining a target location of the first brain region of said patient, said target location being identified, at least in part, based upon the result data of the at least one modeled functional connection measure value, said at least one modeled functional connection measure value statistically measuring interaction of the first brain region and the at least second brain region, wherein the first brain region is a division within a left dorsolateral prefrontal cortex and the at least second brain region is a division within a cingulate region;

d. adjusting at least one transcranial magnetic stimulator used to provide a magnetic stimulation signal for stimulation of the target location to treat the patient, wherein the magnetic stimulation signal is provided by at least one transcranial magnetic stimulator; and e. providing the magnetic stimulation signal by the at least one transcranial magnetic stimulator during an interval of a treatment therapy.

2. The method of claim 1 wherein the at least second brain region further comprises at least a third brain region which is an insula.

3. The method of claim 1 wherein the neuroimaging data comprises functional neuroimaging data and the target location of the first brain region is selected due to the modeled functional connection measure value with the at least second brain region being evaluated as abnormal.

4. The method of claim 3 wherein the functional neuroimaging data undergoes correlation analysis to determine correlated activity between the first brain region and the at least second brain region.

5. The method of claim 3 wherein the functional neuroimaging data is submitted to voxelwise correlation analysis.

6. The method of claim 3 wherein the functional neuroimaging data is submitted to partial least squares analysis.

7. The method of claim 3 wherein the functional neuroimaging data is submitted to path analysis.

8. The method of claim 3 wherein the functional neuroimaging data is used to generate connectivity coefficients between areas of the first and the at least second brain regions.

9. The method of claim 3 wherein the functional neuroimaging data is used to generate measurements of network interaction between areas of the first and the at least second brain regions.

10. The method of claim 1 wherein the neuroimaging data comprises functional neuroimaging data and the target location of a first brain region is identified using the modeled functional connection measure value with the at least second brain region that meets at least one treatment criterion such that a modeled connectivity value is below a specified value.

11. The method of claim 1 wherein the neuroimaging data comprises both structural data and functional data which are both used to determine a target area in the first brain region that interacts with a second target area.

12. The method of claim 1 wherein the unwanted symptom is related to a mood disorder which is depression.

13. The method of claim 1 wherein the unwanted symptom is related to a mood disorder which is bipolar disorder.

14. The method of claim 1 wherein the unwanted symptom is related to a mood disorder which includes symptoms of depression.

15. The method of claim 1 wherein the neuroimaging data comprises functional neuroimaging data and the modeled functional connection measure value is from the selected brain network model and is used to determine the target location of the first brain region that has a connectivity coefficient value with the at least second brain region that meets at least one treatment criterion compared to a reference value.

16. The method of claim 1 wherein the cingulate region is an anterior cingulate cortex.

17. The method of claim 1 wherein the cingulate region includes a subgenual cingulate region.

18. The method of claim 1 wherein the modeled functional connection measure value of the first brain region to the at least second brain region of said patient is abnormal.

19. The method of claim 1 wherein the modeled functional connection measure value is calculated as part of the selected brain network model used to determine the target location of the first brain region that has a modeled functional connection with the at least second brain region and the modeled functional connection value is below a specified value.

20. The method of claim 1 wherein the magnetic stimulation signal is provided to the target location to treat the patient by causing a change in correlation of activity of the at least second brain region with activity in the first brain region.

21. The method of claim 1 wherein the magnetic stimulation signal is provided to the target location to treat the patient by normalizing a measure value for the first brain region and the at least second brain region of the selected brain network model of the patient.

22. A method of guiding the provision of targeted magnetic neurostimulation of a patient suffering an unwanted symptom comprising:

a. using evaluated neuroimaging data that is magnetic resonance imaging data sensed from the brain of a patient for treatment of a patient during a treatment session, said using of said evaluated neuroimaging data includes obtaining from a processor a processor calculated result data for at least one modeled functional connection measure value, said at least one modeled functional connection measure value statistically measuring interaction of a selected brain network model having a first brain region and at least a second brain region of said patient based upon said neuroimaging data;

b. identifying a target location of the first brain region of said patient, said target location being at least in part based upon the processor calculated result data of at least one modeled functional connection measure value of the first brain region to the at least second brain region, wherein the first brain region is a division within a left dorsolateral prefrontal cortex and the at least second brain region is a division within a cingulate region;

c. providing said target location for guiding the adjustment of at least one transcranial magnetic stimulator for generating a treatment magnetic stimulation signal for stimulation of the target location to treat the patient during the treatment session; and, d. providing the magnetic stimulation signal by the at least one transcranial magnetic stimulator during an interval of said treatment session.

23. The method of claim 22 wherein the at least second brain region further comprises at least a third brain region which is an insula.

24. The method of claim 22 wherein the neuroimaging data comprises functional neuroimaging data and the target location of the first brain region is selected due to the modeled functional connection measure value with the at least second brain region that is abnormal.

25. The method of claim 24 wherein the functional neuroimaging data undergoes correlation analysis to determine correlated activity between the first brain region and the at least second brain region.

26. The method of claim 22 wherein the cingulate region is an anterior cingulate cortex.

27. The method of claim 22 wherein the cingulate region includes a subgenual cingulate region.

28. The method of claim 22 wherein the unwanted symptom is related to a mood disorder which includes symptoms of depression.

* * * * *